United States Patent
Long et al.

(10) Patent No.: US 10,137,430 B2
(45) Date of Patent: *Nov. 27, 2018

(54) ALKYLAMINE FUNCTIONALIZED METAL-ORGANIC FRAMEWORKS FOR COMPOSITE GAS SEPARATIONS

(71) Applicant: THE REGENTS OF THE UNIVERSITY OF CALIFORNIA, Oakland, CA (US)

(72) Inventors: Jeffrey R. Long, Oakland, CA (US); Thomas M. McDonald, Berkeley, CA (US); Deanna M. D'Alessandro, Sydney (AU)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/820,350

(22) Filed: Nov. 21, 2017

(65) Prior Publication Data

US 2018/0169613 A1 Jun. 21, 2018

Related U.S. Application Data

(60) Division of application No. 15/373,426, filed on Dec. 8, 2016, now Pat. No. 9,861,953, which is a (Continued)

(51) Int. Cl.
*B01D 53/02* (2006.01)
*B01D 53/04* (2006.01)
(Continued)

(52) U.S. Cl.
CPC ............ *B01J 20/226* (2013.01); *B01D 53/02* (2013.01); *B01D 53/62* (2013.01);
(Continued)

(58) Field of Classification Search
None
See application file for complete search history.

(56) References Cited

U.S. PATENT DOCUMENTS

| 6,547,854 B1 | 4/2003 | Gray |
| 7,288,136 B1 | 10/2007 | Gray |

(Continued)

FOREIGN PATENT DOCUMENTS

| CA | 2867284 A1 | 9/2013 |
| CN | 101151091 A | 3/2008 |

(Continued)

OTHER PUBLICATIONS

Korean Intellectual Property Office (KIPO), International Search Report and Written Opinion dated Mar. 22, 2013, related PCT International Application No. PCT/US2012/060915, pp. 1-10, with claims searched, pp. 11-14.

(Continued)

*Primary Examiner* — Daniel Berns
(74) *Attorney, Agent, or Firm* — O'Banion & Ritchey LLP; John P. O'Banion

(57) ABSTRACT

Functionalized metal-organic framework adsorbents with ligands containing basic nitrogen groups such as alkylamines and alkyldiamines appended to the metal centers and method of isolating carbon dioxide from a stream of combined gases and carbon dioxide partial pressures below approximately 1 and 1000 mbar. The adsorption material has an isosteric heat of carbon dioxide adsorption of greater than −60 kJ/mol at zero coverage using a dual-site Langmuir model.

21 Claims, 11 Drawing Sheets

Related U.S. Application Data continuation of application No. 14/228,532, filed on Mar. 28, 2014, now abandoned, which is a continuation of application No. PCT/US2012/060915, filed on Oct. 18, 2012.

(60) Provisional application No. 61/548,676, filed on Oct. 18, 2011.

(51) Int. Cl.

| | | |
|---|---|---|
| *B01D 53/047* | (2006.01) | |
| *B01D 53/40* | (2006.01) | |
| *B01D 53/80* | (2006.01) | |
| *B01D 53/81* | (2006.01) | |
| *B01D 53/96* | (2006.01) | |
| *B01J 20/22* | (2006.01) | |
| *B01J 20/28* | (2006.01) | |
| *B01D 53/62* | (2006.01) | |
| *B01J 20/34* | (2006.01) | |
| *C07F 1/08* | (2006.01) | |

(52) U.S. Cl.
CPC ..... *B01J 20/28057* (2013.01); *B01J 20/3425* (2013.01); *B01J 20/3483* (2013.01); *C07F 1/08* (2013.01); *B01D 2253/204* (2013.01); *B01D 2257/504* (2013.01); *B01D 2258/0283* (2013.01); *Y02A 50/2342* (2018.01); *Y02C 10/04* (2013.01); *Y02C 10/08* (2013.01)

(56) References Cited

U.S. PATENT DOCUMENTS

| 9,861,953 | B2 | 1/2018 | Long |
|---|---|---|---|
| 2008/0121105 | A1 | 5/2008 | Schubert |
| 2010/0154635 | A1 | 6/2010 | Schubert |
| 2011/0104213 | A1 | 5/2011 | Rosi |
| 2012/0070353 | A1 | 3/2012 | Trukhan |

FOREIGN PATENT DOCUMENTS

| WO | 2010106133 A1 | 9/2010 |
|---|---|---|
| WO | 2010148276 A2 | 12/2010 |
| WO | 2013059527 A1 | 4/2013 |
| WO | 2013144628 | 10/2013 |

OTHER PUBLICATIONS

McDonald, Thomas M. et al., "Enhanced carbon dioxide capture upon incorporation of N,N'-dimethylethylenediamine in the metal-organic framework CuBTTri," Chem. Sci., Aug. 2, 2011, vol. 2, pp. 2022-2028.

European Patent Office (EPO), European Supplemental Search Report dated May 8, 2015, related EP Application No. 12841410.9, pp. 1-10, with claims searched, pp. 11-13.

McDonald, Thomas M. et al., "Capture of Carbon Dioxide from Air and Flue Gas in the Alkylamine-Appended Metal-Organic Framework mmen-Mg2(dobpdc)", Journal of the American Chemical Society, 2012, 134 (16), pp. 7056-7065, Apr. 4, 2012.

Korean Intellectual Property Office (KIPO), International Search Report and Written Opinion, dated Jul. 24, 2015, related PCT International Application No. PCT/US2015/027165, pp. 1-14, with claims searched, pp. 15-19.

McDonald, Thomas M. et al., "Cooperative insertion of CO2 in diamine-appended metal-organic frameworks", Nature, Mar. 19, 2015, (Epub. Mar. 11, 2015), vol. 519, No. 7543, pp. 303-308.

Demessence et al., "Strong CO2 Binding in a Water-Stable, Triazolate-Bridged Metal-Organic Framework Functionalized with Ethylenediamine", J. Am. Chem. Soc. (2009), vol. 131, pp. 8784-8786 (published online Jun. 8, 2009).

Demessence et al., Supporting Information for "Strong CO2 Binding in a Water-Stable, Triazolate-Bridged Metal-Organic Framework Functionalized with Ethylenediamine", J. Am. Chem. Soc. (2009), vol. 131, pp. 8784-8786 (published online Jun. 8, 2009).

Hwang et al., "Amine Grafting on Coordinatively Unsaturated Metal Centers of MOFs: Consequences for Catalysis and Metal Encapsulation", Angew. Chem. Int. Ed. 2008, 47, 4144-4148 (published online Apr. 24, 2008).

Hwang et al., Supporting Information for "Amine Grafting on Coordinatively Unsaturated Metal Centers of MOFs: Consequences for Catalysis and Metal Encapsulation", Angew. Chem. Int. Ed. 2008, 47, 4144-4148 (published online Apr. 24, 2008).

European Patent Office (EPO), Communication (ESSR) dated Oct. 27, 2017, related European patent application No. 15782401.2, pp. 1-7, with claims searched, pp. 8-10.

State Intellectual Property Office of the People's Republic of China (SIPO), The First Office Action dated Jul. 4, 2018, related Chinese patent application No. 201580030107.3, Chinese language document pp. 1-11, English language translation pp. 12-25, claims examined pp. 26-30.

ALKYLAMINE FUNCTIONALIZED METAL-ORGANIC FRAMEWORKS FOR COMPOSITE GAS SEPARATIONS

CROSS-REFERENCE TO RELATED APPLICATIONS

This application is a division of U.S. patent application Ser. No. 15/373,426 filed on Dec. 8, 2016, incorporated herein by reference in its entirety, which is a continuation of U.S. patent application Ser. No. 14/228,532 filed on Mar. 28, 2014, incorporated herein by reference in its entirety, which is a 35 U.S.C. § 111(a) continuation of PCT international application number PCT/US2012/060915 filed on Oct. 18, 2012, incorporated herein by reference in its entirety, which claims priority to and the benefit of U.S. provisional patent application Ser. No. 61/548,676 filed on Oct. 18, 2011, incorporated herein by reference in its entirety. Priority is claimed to each of the foregoing applications.

The above-referenced PCT international application was published as PCT International Publication No. WO 2013/059527 on Apr. 25, 2013, incorporated herein by reference in its entirety.

STATEMENT REGARDING FEDERALLY SPONSORED RESEARCH OR DEVELOPMENT

This invention was made with Government support under DE-SC0001015 awarded by the Department of Energy. The Government has certain rights in the invention.

INCORPORATION-BY-REFERENCE OF MATERIAL SUBMITTED IN A COMPUTER PROGRAM APPENDIX

Not Applicable

BACKGROUND OF THE INVENTION

1. Field of Invention

This invention pertains to the use of metal-organic frameworks as adsorbents for the separation of composite gasses, and more particularly to adsorbents with a high concentration of alkylamine functionalized sites in a metal organic framework and methods for the separation of a variety of materials based on selective, reversible electron transfer reactions. For example, methods are provided for the separation of individual gases from as stream of combined gases such as $CO_2$ from $N_2$ gases or $CO_2$ from $H_2$ gases from a stream of combined gases.

2. Background

There is a continuing need for the efficient separation of gas mixtures into their component parts in many different industrial processes including energy production and emission reduction. Many gas separations are presently performed on large scales in numerous industrial processes, often at significant cost.

For example, the production of syngas from the conversion of fossil fuels (natural gas, coal, oil, oil shale, etc) or biomass requires the separation of $CO_2$ from $H_2$ and other useful gasses. In this context, the coal or other material is converted into syngas (CO and $H_2$) which subsequently undergoes the water-gas shift reaction to generate $CO_2$ and $H_2$. The hydrogen is used to generate electricity after it is separated from $CO_2$, which can then be prevented from release into the atmosphere. This strategy, called pre-combustion $CO_2$ capture, is advantageous in comparison to other $CO_2$ capture technologies that require separation of $CO_2$ from $N_2$, $O_2$, or $CH_4$ because the differences in size and polarizability between $CO_2$ and $H_2$ can be exploited.

Separation of $CO_2$ from $CH_4$ is also relevant to the purification of natural gas, which can have impurity levels of up to 92% $CO_2$ at its source. Carbon dioxide removal is required for approximately 25% of the natural gas reserves in the United States. Removal of $CO_2$, which is most commonly accomplished using amines to reduce $CO_2$ levels to the required 2% maximum, is conducted at pressures between 20 bar and 70 bar. Carbon dioxide removal is required for approximately 25% of the natural gas reserves in the United States.

Gas separations are also important in post-combustion of fossil fuels for energy production. The combustion of fossil fuels is largely responsible for the increase in the global concentration of $CO_2$ in the Earth's atmosphere, yet fossil fuels will continue to be heavily utilized for energy production during the 21st century.

The development of more efficient processes for capturing $CO_2$ from power plant flue streams is critical for the reduction of greenhouse gas emissions implicated in global warming. Currently, there is significant interest in the development and implementation of technologies that slow $CO_2$ emissions and thus forestall the most severe consequences of global warming. For limiting future $CO_2$ emissions from large, stationary sources like coal-fired power plants, carbon capture and sequestration (CCS) has been proposed. The CCS process involves the selective removal of $CO_2$ from gas mixtures, the compression of pure $CO_2$ to a supercritical fluid, transportation to an injection site, and finally permanent subterranean or submarine storage. For the retrofit of existing power plants, post-combustion $CO_2$ capture is a likely configuration. In this design, fuel is burned in air and $CO_2$ is removed from the effluent. For coal-fired power plants, the largest flue gas components by volume are $N_2$ (70-75%), $CO_2$ (15-16%), $H_2O$ (5-7%) and $O_2$ (3-4%), with total pressures near 1 bar and temperatures between 40° C. and 60° C. For post-combustion $CO_2$ capture, maximizing adsorption capacity for $CO_2$ at low pressures is highly desirable. Because the partial pressure of $CO_2$ in flue gas emitted from coal fired power stations is typically between 0.10 and 0.15 bar, the simplest approximation for the capacity of materials being considered is the quantity of gas adsorbed at these lower pressures, not the capacity at 1 bar.

Aqueous amine solutions are currently the most viable adsorbents for carbon capture and are presently used for the removal of $CO_2$ from industrial commodities like natural gas. While a variety of advanced amines are available, 30% monoethanolamine (MEA) in water is the benchmark solvent against which competing technologies are generally compared. The low solvent cost and proven effectiveness make MEA an attractive adsorbent for many applications.

Conventional $CO_2$ capture processes involving the chemisorption of $CO_2$ by alkylamine-containing liquids present several disadvantages, including the considerable heat required to regenerate the liquid, solution boil-off and the necessary use of inhibitors for corrosion control. Therefore, if MEA were to be utilized for carbon capture and sequestration, electricity prices are projected to increase by 86%.

The formation of ammonium carbamate from two MEA molecules and one $CO_2$ molecule endows the scrubber with extremely high selectivity for $CO_2$, but significant energy is required to regenerate the solution. This high regeneration energy cost has two primary components: first, the strong, chemisorptive bond between the carbon dioxide and the amine must be broken; second, a large amount of spectator water solvent must be heated and cooled along with the active amine adsorbent, giving rise to an inefficient system. Because amines are corrosive to plant infrastructure, solutions are typically limited to no more than 30% (w/w) of the amine, and a significant increase in this concentration is not deemed feasible. In addition, solvent boil-off occurs during repeated regeneration cycles consuming the scrubber and increasing costs. The diversion of steam from the electricity generation cycle to the solvent regeneration cycle sharply reduces the net electricity output of the plant, drastically increasing electricity costs. It has been demonstrated that plant efficiency is highly dependent on the solvent regeneration energy that is needed. These limitations represent the most significant obstacles to wider implementation of amine scrubbing technologies for post-combustion carbon capture.

Attempts to address these limitations have focused on the adsorption of $CO_2$ in porous solids such as zeolites and amine-modified silicas via the formation of carbamate or bicarbonate species. The viability of the materials under realistic flue stream conditions requires air and water stability, corrosion resistance, high thermal stability, and high selectivity for $CO_2$ over other components in flue gas. Currently, aqueous amines are used industrially to separate $CO_2$ from gas mixtures with high $CO_2$ partial pressures like natural gas, while some solid adsorbents are used to remove $CO_2$ from mixtures with low $CO_2$ partial pressures. In addition to the separation of combustion gases, there are a number of current industrial processes that utilize liquid or solid adsorbents to remove $CO_2$ from gas mixtures.

Accordingly, there is a need for an efficient methods and materials for selectively separating constituent gases from a stream of gases that can be performed at lower temperatures and pressures than existing techniques. There is also a need for materials and methods that provide selective, reversible electron transfer reactions and associated functions such as catalysis, including oxidation as well as gas storage. The present invention satisfies these needs as well as others and is generally an improvement over the art.

SUMMARY OF THE INVENTION

The present invention is directed to metal-organic framework materials and methods for use in a variety of gas separation and manipulation applications including the isolation of individual gases from a stream of combined gases, such as carbon dioxide/nitrogen, carbon dioxide/hydrogen, carbon dioxide/methane, carbon dioxide/oxygen, carbon monoxide/nitrogen, carbon monoxide/methane, carbon monoxide/hydrogen, hydrogen sulfide/methane and hydrogen sulfide/nitrogen.

Among the primary benefits of physiorption onto solid materials is the low regeneration energy compared to that required for aqueous amines. However, this benefit frequently comes at the expense of low capacity and poor selectivity. The present invention provides adsorbents that bridge the two approaches through the incorporation of sites that bind $CO_2$ by chemisorption onto solid materials. The new materials may eliminate the need for aqueous solvents, and may have significantly lower regeneration costs compared with traditional amine scrubbers, yet maintain their exceptional selectivity and high capacity for $CO_2$ at low pressures.

The adsorption materials for gas separations are metal-organic frameworks containing ligands with basic nitrogen groups. Metal-organic frameworks are porous, crystalline solids that are preferably functionalized with the incorporation of alkylamines, which exhibit enhanced basicity over aromatic amines and are capable of strongly adsorbing acid gases.

The preferred metal-organic frameworks are a group of porous crystalline materials formed of metal cations or clusters joined by multitopic organic linkers. By way of example, and not of limitation, the invention provides functional materials made from metal-organic framework adsorbents with a framework selected from the group: M-BTT (M=Ca, Fe, Mn, Cu, Co, Ni, Cr, Cd); M-BTTri (M=Cr, Mn, Fe, Co, Ni, Cu); M-BTP (M=Co, Ni, Zn); $M_3(BTC)_2$ (M=Cu, Cr); $M_2$(dobdc) (M=Mg, Ca, Mn, Cr, Fe, Co, Ni, Cu, Zn); $M_2$(dobpdc) (M=Mg, Ca, Mn, Cr, Fe, Co, Ni, Cu, Zn), and MIL-100 (M=Fe, Al, Cr, Ti, Sc, V); MIL-101 (M=Fe, Al, Cr, Ti, Sc, V). The metal-organic framework may also include open metal sites.

Ligands of the metal-organic framework may contain other structural elements used to coordinate the ligand to one or more metals of the framework. These include but are not limited to the following functional groups: carboxylate, triazolate, pyrazolate, tetrazolate, pyridines, amines, alkoxide and/or sulfate groups. The preferred alkylamine ligand is N,N'-dimethylethylenediamine ("mmen") producing (mmen-$Mg_2$-BTTri) or mmen-$Mg_2$.(dopbdc) functionalized frameworks.

The removal of dilute concentrations of acid gases by highly selective adsorption, as demonstrated by the affinity of (mmen-CuBTTri) for $CO_2$ versus $N_2$, is used to illustrate the use of the adsorbents in post-combustion $CO_2$ capture applications as well as other gas separation applications.

The basic nitrogen groups may be incorporated into the framework on a ligand prior to framework formation, through substitution or modification of a functional group that was bonded to a ligand prior to framework formation, or by substitution of a ligand after framework formation with the ligand with a basic nitrogen group.

Due to their high surface areas and low bulk densities, these materials demonstrate remarkable working capacities for sequestering carbon dioxide, making them ideal for use in large scale processing plants and a great improvement over current adsorbents. The successful implementation of these new adsorbents could reduce the substantial energy cost of adsorbing $CO_2$ emissions resulting from the combustion of fossil fuels, including coal and natural gas.

Another embodiment is a method of separating a mixture stream comprising $CO_2$ and $N_2$. The method includes contacting the mixture stream including $CO_2$ and $N_2$ with a material comprising a metal-organic framework, and a ligand with a basic nitrogen group, wherein the material preferably has an isosteric heat of $CO_2$ adsorption of greater than −70 kJ/mol at zero coverage as determined by the Clausius-Clapeyron relation, obtaining a stream richer in $CO_2$ as compared to the mixture stream, and obtaining a stream richer in $N_2$ as compared to the mixture stream.

According to one aspect of the invention, a process is provided for attaching polyamine ligands to the surface of metal-organic frameworks with exposed metal cations for use in $CO_2$ capture.

Another aspect of the invention is to provide a porous adsorbent material with a metal organic framework functionalized with N,N'-dimethylethylenediamine ("mmen") with frameworks of the family M-BTTri where M=(Cr, Mn, Fe, Co, Ni or Cu) with $H_3[(Cu_4Cl)_3(BTTri)_8$ (mmen)$_{12}]$ particularly preferred for the separation of gases from a mixture of gases at low pressures below approximately 1 bar.

According to another aspect of the invention, a functionalized metal organic framework is provided that can separate gases at low temperatures and pressures.

Yet another aspect of the invention is to provide a material and method for pre-combustion separation of carbon dioxide and hydrogen and methane from a stream of gases.

A further aspect of the invention is to provide a material and method for separation of carbon dioxide from a stream of post-combustion flue gases at low pressures and concentrations.

Another aspect of the invention is to provide a metal-organic framework that is adaptable to many different separation needs.

Further aspects of the invention will be brought out in the following portions of the specification, wherein the detailed description is for the purpose of fully disclosing preferred embodiments of the invention without placing limitations thereon.

BRIEF DESCRIPTION OF THE DRAWINGS

The invention will be more fully understood by reference to the following drawings which are for illustrative purposes only.

DETAILED DESCRIPTION OF THE INVENTION

Figure 1:
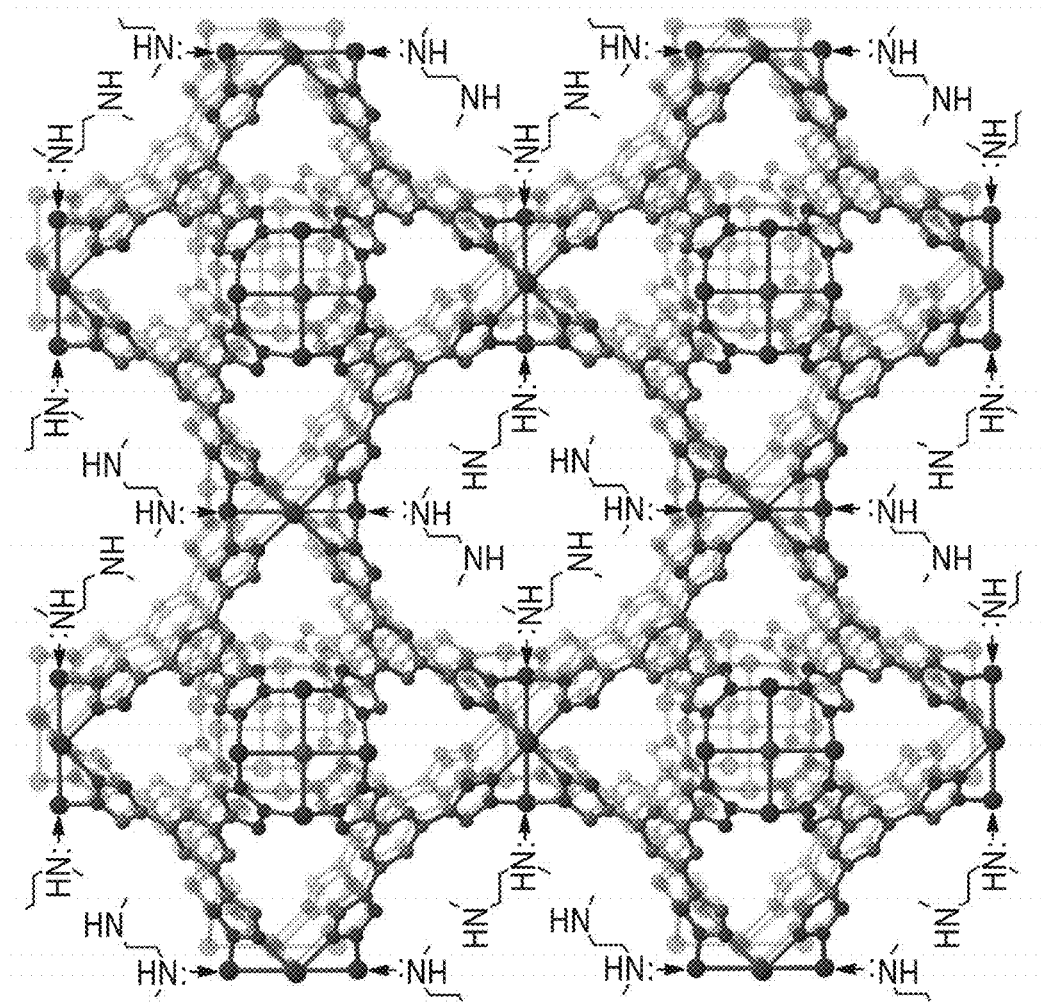
FIG. 1 is a representation of a portion of the structure of the amine functionalized metal-organic framework mmen-CuBTTri, with incorporation of the diamine N,N'-dimethylethylenediamine onto open metal sites within the pores according to the invention.

Referring more specifically to the drawings, for illustrative purposes several embodiments of the metal-organic framework adsorbents of the present invention are depicted generally in FIG. 1 through FIG. 9 and the associated methods for using and producing the alkylamine functionalized frameworks. It will be appreciated that the methods may vary as to the specific steps and sequence and the metal-organic framework architecture may vary as to structural details, without departing from the basic concepts as disclosed herein. The method steps are merely exemplary of the order that these steps may occur. The steps may occur in any order that is desired, such that it still performs the goals of the claimed invention.

Metal-organic frameworks are a class of porous, crystalline adsorbents that enables greater functionality with reduced adsorbent mass and volume compared to traditional solid adsorbents. These metal-organic frameworks are preferred because of the presence of coordinatively unsaturated metal centers (open metal sites) along the pore surfaces. These coordinate metal cations are known to behave as Lewis acids that strongly polarize gas adsorbents and are further amenable to post-synthetic functionalization. In these frameworks with well separated open metal sites, one amine of a diamine ligand molecule can bind to a metal cation as a Lewis base while the second amine remains available as a chemically reactive adsorption site. The metals in the framework can be individual metal atoms bridged by a set of ligands or metal clusters (a collection of metal atoms that as a group interact with a set of ligands.

The preferred metal-organic frameworks are a group of porous crystalline materials formed of metal cations or clusters joined by multitopic organic linkers. These are frequently frameworks that are described as having "open metal sites" (also called coordinatively unsaturated metal centers).

By way of example, and not of limitation, the invention provides functional materials made from metal-organic framework adsorbents selected from the group: M-(1,3,5-benzenetristriazolate) where (M=Cr, Mn, Fe, Co, Ni or Cu,). Other basic framework examples that can be functionalized with alkylamines and used for low pressure applications include: M-BTT (M=Ca, Fe, Mn, Cu, Co, Ni, Cr, Cd) (BTT=1,3,5-benzenetristetrazolate): M-BTP where (M=Co, Ni, Zn) and (BTP=1,3,5-benzenetrispyrazolate); $M_3$(BTC)$_2$ where (M=Cu, Cr) and (BTC=1,3,5-benzenetriscarboxylate); $M_2$(dobdc) where (M=Mg, Ca, Mn, Cr, Fe, Co, Ni, Cu, Zn) and (dobdc=2,5-dioxido-1,4-benzenedicarboxylate); $M_2$(dobpdc) where (M=Mg, Ca, Mn, Cr, Fe, Co, Ni, Cu, Zn) and (dobpdc=4,4'-dioxido-3,3'-biphenyldicarboxylate); MIL-100 where (M=Fe, Al, Cr, Ti, Sc, V) and (Ligand=BTC=1,3,5-benzenetriscarboxylate); and MIL-101 where (M=Fe, Al, Cr, Ti, Sc, V) and (Ligand=BDC=1,4-benzenedicarboxylate).

The ligands of the metal-organic frameworks preferably contain basic nitrogen groups. These basic nitrogen ligands may include, for example, alkyl amines or imines, but not aromatic amines (i.e. aniline derivatives).

Some or all ligands of the metal-organic framework include functional groups that are not coordinated to metal cations and are available to form reversible weak chemical bonds with $CO_2$. Preferably, the reactive chemical atom contains a lone pair of electrons including nitrogen, oxygen, sulfur, and phosphorous. More preferably, it is a basic amine. More preferably, the lone pair or pairs of the reactive atom are not in resonance with an aromatic ring. Most preferably, the functional group is a primary, secondary, or tertiary alkylamine (an aliphatic amine).

Ligands of the metal-organic framework may contain other structural elements used to coordinate the ligand to one or more metals of the framework. These include but are not limited to the following functional groups: carboxylate, triazolate, pyrazolate, tetrazolate, pyridines, amines, alkoxide and/or sulfate groups. The preferred alkylamine ligand is N,N'-dimethylethylenediamine ("mmen") producing (mmen-$Mg_2$-BTTri) or mmen-$Mg_2$.(dopbdc) functionalized frameworks.

Some or all ligands of the metal organic framework may contain one or more aromatic rings that contain carbon and may contain other atoms including boron, nitrogen, and oxygen. This is most preferably five and six membered rings. These rings may provide structural rigidity to the material and/or provide spatial separation of other functional groups contained within ligands as to provide porosity to the adsorbent.

The structure of the basic ligands may include three distinct components: 1) A backbone that provides structural rigidity to the material. This may be, for example, an aromatic group such as a phenyl group. 2) At least one functional group that binds the ligands to the metal such as nitrogen or oxygen atoms. Specific examples include a carboxylate group, a triazolate group (as in this case for Cu-BTTri), pyrazolates, tetrazolates, pyridines, and sulfates. 3) A functional group that contains a nitrogen atom that is not integral to the structural rigidity of the material and is not bound to a metal that is available to interact with gases.

The functional group that contains a nitrogen atom and interacts with the $CO_2$ molecule is preferably a basic organic group. Preferred functional groups include primary amines, secondary amines, tertiary amines, primary imines, and secondary imines, and similar compounds. Although these groups all contain nitrogen, in alternative embodiments, these groups could include other atoms as well, especially atoms having an available lone pair of electrons.

These basic nitrogen functional groups can be incorporated into the metal-organic framework in one of three preferable ways: 1) attached as a functional group on a ligand prior to framework formation; 2) as a substitution or modification of a functional group that was bonded to a ligand prior to framework formation; and 3) as a substitution of a ligand after framework formation for a new ligand that contains the desired functional group.

If the amines are attached to the ligand prior to framework formation as in method 1) described above, for incorporating a basic nitrogen group into the framework, the nitrogen is preferably not directly bonded to an aromatic carbon atom. This is because the nitrogen would be bonded to an alkylcarbon (a methylene), giving rise to an alkylamine groups, which is preferred. Accordingly, it is preferred that at least one atom of any type separates the amine that interacts with $CO_2$ from the aromatic backbone.

In method 2), the basic nitrogen groups are incorporated into the framework through a substitution or modification of a functional group that was bonded to a ligand prior to framework formation and the ligands are not exchanged. Rather, functional groups within the ligands may be exchanged for the desired functionality. This could potentially include modification of C—H bonds by aromatic substitution reactions, nucleophilic substitution reactions (including replacement of alkyl halide groups for alkyl amine groups), condensation reactions (including conversions of aldehydes to imines), and reductions (including imines to alkyl amines, nitriles to alkylamines, and amides to alkyl amines). Other potential reactions could also be used that modify ligands to include alkylamines or imines after framework synthesis.

Finally, with method 3) for incorporating a basic nitrogen group into the framework, the metal ligands are exchanged. The new ligand preferably has at least two functional groups: 1) A functional group used to bind CO2 and 2) a functional group used to bind to the metal. The second functional group that binds the metal can also be an amine. It is possible to use other functional groups such as oxygen containing groups like alcohols, ethers or alkoxides, carbon groups like carbenes or unsaturated bonds like alkenes or alkynes, or sulfur atoms.

Preferable characteristic for the end that binds the metal include the following: 1) strongly bonded to the metal so the functional groups are not removed upon framework activation by vacuum; 2) capable of being grafted at nearly all metal sites within the pores for nearly complete functionalization. The ligand itself may contain one or more amines that bind $CO_2$. For example, the ligand could have 3 carboxylate groups for binding metals and 1, 2, or 3 (or more) alkylamine groups on each ligand. Examples may include Tris(2-aminoethyl)amine (primary and tertiary amines) or Tris[2(methylamino)ethyl]amine (secondary and tertiary amines), which would be capable of binding a metal-site with one amine and adsorbing $CO_2$ with 3 other amines. These examples are branched.

Other alternatives are linear like tetraethylenepentamine (2 primary amines and 3 tertiary amines) or Diethylenetriamine (2 primary amines and 1 secondary amine). In the case of mmen-CuBTTri, described herein, it is believed that each amine binds one $CO_2$. However, it is also possible for two or more amines to bind a single $CO_2$, especially in ligands with multiple amines.

Amines do not necessarily simply polarize $CO_2$; rather, they strongly and selectively bind it through chemisorptive interactions. Amines tethered to solid surfaces within porous materials also have considerable advantages over aqueous alkanolamines. It has also been found that the incorporation of alkylamine groups at higher loadings can further polarize the overall surface area of a metal-organic framework, thereby increasing the capacity for $CO_2$ capture. Other functional groups are similarly capable of polarizing framework surfaces, but many are not capable of undergoing the chemisorptive type process. Higher order amines, in particular secondary amines, have more favorable adsorption characteristics in solutions as well as on solid adsorbents. It has been found that the incorporation of N,N'-dimethylethylenediamine (mmen) at high loadings within CuBTTri affords a material with exceptional $CO_2$ capture characteristics.

Generally, a method for separating constituent gases from stream of mixed gases containing at least a first gas and a second gas is provided with the use of an adsorbent of a metal-organic framework adsorbent of the group M-BTT (M=Ca, Fe, Mn, Cu, Co, Ni, Cr, Cd); M-BTTri (M=Cr, Mn, Fe, Co, Ni, Cu); M-BTP (M=Co, Ni, Zn); $M_3(BTC)_2$ (M=Cu, Cr); $M_2$(dobdc) (M=Mg, Ca, Mn, Cr, Fe, Co, Ni, Cu, Zn); $M_2$(dobpdc) (M=Mg, Ca, Mn, Cr, Fe, Co, Ni, Cu, Zn); MIL-100 (M=Fe, Al, Cr, Ti, Sc, V) or MIL-101 (M=Fe, Al, Cr, Ti, Sc, V) that have been functionalized with ligands containing basic nitrogen groups including but not limited to alkyldiamine ligands. The stream of mixed gases is directed across a bed of adsorbent and the molecules of the first gas are adsorbed onto the metal-organic framework so that the resulting stream is richer in the second gas as compared to the mixture stream that is collected. The adsorbed first gas is released from the metal-organic framework to obtain a stream richer in the first chemical as compared to the mixture stream that is also collected. The adsorbed chemical is typically released by a change in temperature or pressure. A purge gas may also be used to move the released gas through the bed for collection.

It will be seen that the selection of the metal cations and organic framework structure can be tailored by the type of gases to be separated and the temperature and pressure conditions of the separation. $M_2$(dobpdc) and CuBTTri functionalized with alkylamines are frameworks that are particularly suited for carbon dioxide/nitrogen gas separations at $CO_2$ partial pressures between 1 and 1000 mbar.

Figure 8A:
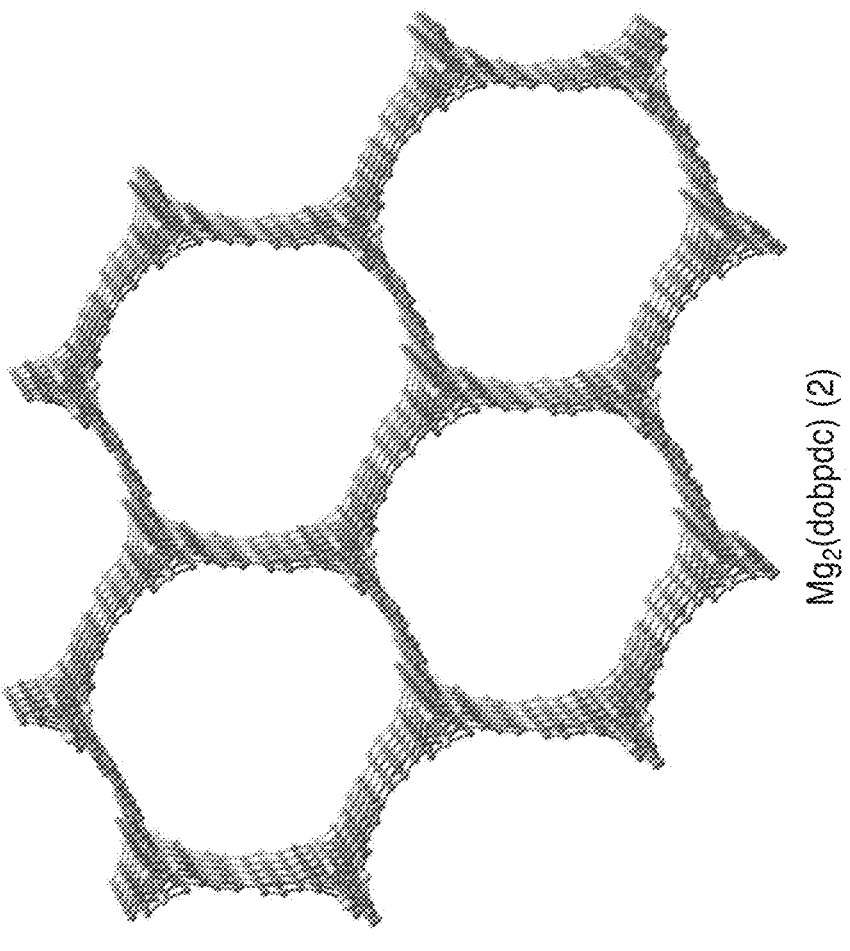
FIG. 8A and FIG. 8B depict a synthesis scheme for mmen-$Mg_2$(dobpdc) where (mmen=N,N'-dimethylethylenediamine) and (dobpdc$^{4-}$=4,4'-dioxido-3,3'-biphenyldicarboxylate). From the microwave reaction of $MgBr_2 \cdot 6H_2O$ and $H_4$dobpdc, $Mg_2$(dobpdc) is obtained following evacuation of the as synthesized solid at high temperatures (middle). Addition of an excess of mmen to the evacuated framework yields the amine-appended $CO_2$ adsorbent $Mg_2$(dobpdc)(mmen)$_{1.6}$($H_2O$)$_{0.4}$.
Figure 8A:
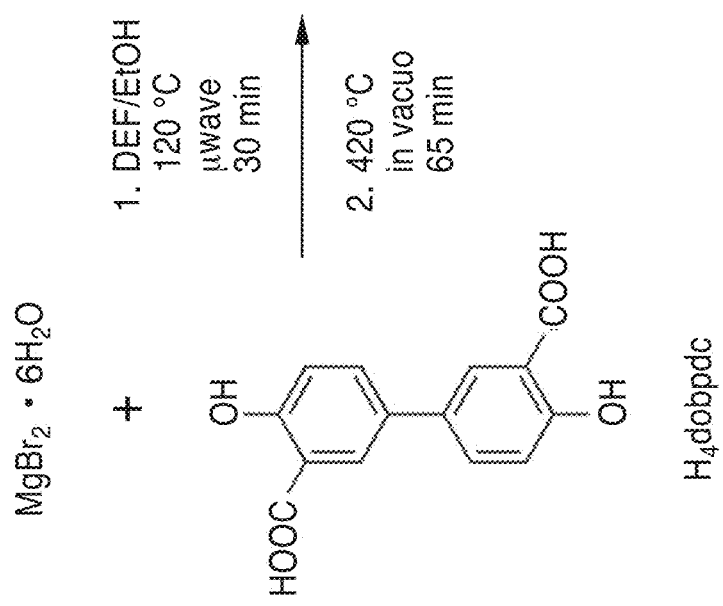
Figure 8B:
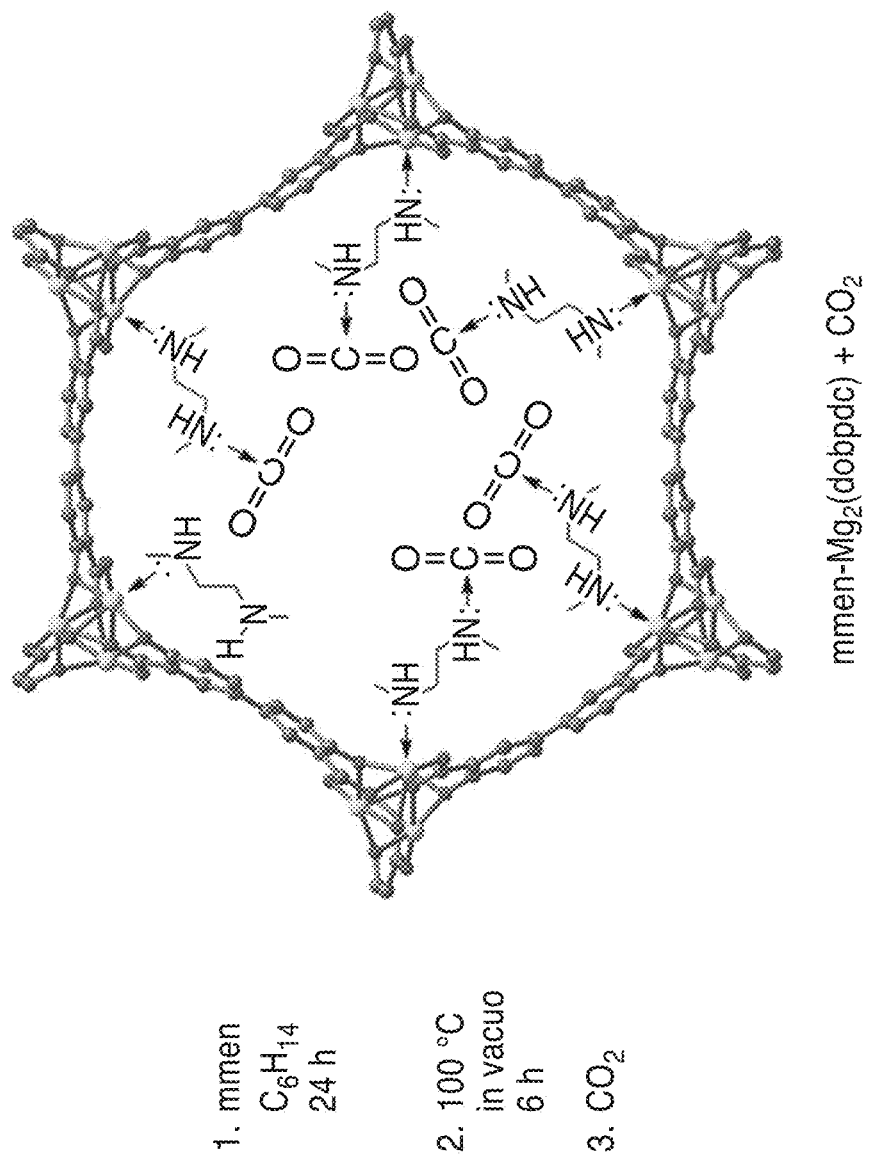
Figure 9:
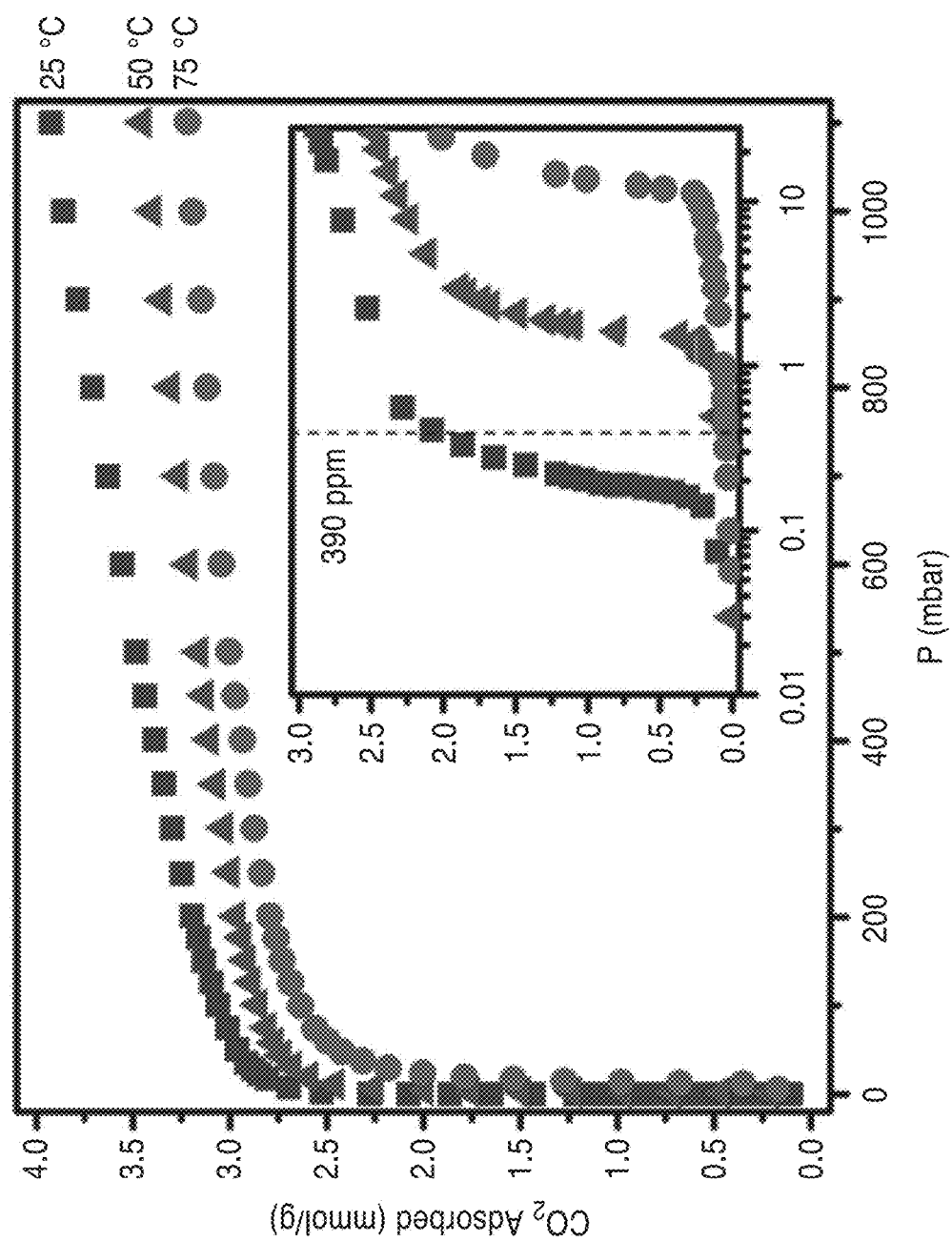
FIG. 9 is a graph of the adsorption of $CO_2$ in mmen-$Mg_2$-(dobpdc) at 25° C. (squares), 50° C. (triangles), and 75° C. (circles). Inset: The isotherms at very low pressures exhibit a step that shifts to higher pressures at higher temperatures. The dashed, vertical line marks the current partial pressure of $CO_2$ in air (390 ppm).

Two frameworks, mmen-CuBTTri shown in FIG. 1 and mmen-$Mg_2$(dobpdc) shown in FIG. 8B, are used to illustrate the M-BTTri and $M_2$(dobpdc) framework families and the methods of use for gas separations.

Turning now to FIG. 1, an embodiment of a portion of a metal-organic framework crystal structure of a mmen-CuBTTri, a water stable, triazolate-bridged framework of the invention is schematically shown. The incorporation of the N,N'-dimethylethylenediamine (mmen) ligand into the (CuBTTri) framework, was shown to drastically enhance $CO_2$ adsorption. The attachment of the mmen alkylamine at the metal centers of the framework is shown with arrows. Because the diamines are shorter than the distance between two adjacent metal sites one amine from each molecule is bound to a single metal site, while the other amine is free to interact with guest gas molecules upon framework activation.

High porosity is maintained despite stoichiometric attachment of mmen to the open metal sites of the framework, resulting in a BET surface area of 870 $m^2/g$. At 25° C. under a 0.15 bar $CO_2$/0.75 bar $N_2$ mixture, mmen-CuBTTri adsorbs 2.38 mmol $CO_2/g$ (9.5 wt %) with a selectivity of 327, as determined using Ideal Adsorbed Solution Theory (IAST). The high capacity and selectivity are consequences of the exceptionally large isosteric heat of $CO_2$ adsorption, calculated to be −96 kJ/mol at zero coverage. Infrared spectra support chemisorptions between amines and $CO_2$ as one of the primary mechanisms of uptake. Despite the large initial heat of adsorption, the $CO_2$ uptake was fully reversible and the framework could be easily regenerated at 60° C., enabling a cycling time of just 27 minutes with no loss of capacity over the course of 72 adsorption/desorption cycles.

Overall, the performance characteristics of CuBTTri indicate it to be an exceptional new adsorbent for $CO_2$ capture, comparing favorably with both amine-grafted silicas and aqueous amine methods.

The large capacity, high selectivity, and fast kinetics of these materials for adsorbing $CO_2$ from dry gas mixtures with $N_2$ and $O_2$ make the functionalized metal-organic frameworks attractive new adsorbents for applications in which zeolites and liquid adsorbents are currently used, including the removal of $CO_2$ from flue gases at low pressures below approximately 1 bar.

The invention may be better understood with reference to the accompanying examples, which are intended for purposes of illustration only and should not be construed as in any sense limiting the scope of the present invention as defined in the claims appended hereto.

Example 1

In order to demonstrate the functionality of metal-organic frameworks featuring coordinatively-unsaturated metal centers for separating gases, a mmen-CuBTTri framework as shown in FIG. 1 was constructed and tested.

A sample of CuBTTri (100.0 mg, 32.4/µmol) was suspended in 10 mL of anhydrous hexane under nitrogen, and 75.4 µL (61.2 µg, 701 µmol, 1.8 equivalents per unsaturated $CU^{II}$ site) of N,N' dimethylethylenediamine (mmen) was added via micropipette with stirring. The compound immediately turned blue and the suspension was heated at reflux for 18 hours under nitrogen. The solid was collected by filtration and washed with successive aliquots of hexane (5×10 mL) to remove unreacted diamine. The solid was then dried under reduced pressure to remove hexane. Anal. Calcd. for $C_{144}H_{195}Cl_3Cu_{12}N_{96}$ (Mw=4139.6 g/mol): C41.78, H4.75, N32.48. Found: C42.23, H4.47, N32.05.

The grafted material, mmen-CuBTTri, was then activated by heating at 50° C. for 24 hours under a dynamic vacuum prior to gas adsorption. Nitrogen adsorption isotherms collected at 77 K indicate a BET surface area of 870 $m^2/g$, while powder x-ray diffraction data show the structure of the CuBTTri framework to be intact. Overall, the characterization data are most consistent with a chemical formula of $H_3[(CU_4Cl)_3(BTTri)_8(mmen)_{12}]$, with approximately one mmen molecule for each available metal site. Thus, mmen-CuBTTri is thought to possess a high concentration of surface-appended mmen molecules, where one of the amine groups is bound to a $Cu^{2+}$ center, while the other dangles within the pore, as depicted in FIG. 1.

Using the same procedure, another framework: $H_3[(Cu_4Cl)_3(BTTri)_8(men)_6].2H_2O$ (men-CuBTTri) was produced and evaluated for comparison. 1.8 equivalents of N-methylethylenediamine (men) was added to activated CuBTTri in hexane, giving rise a blue material. Anal. Calcd. for $C_{114}H_{115}C_{13}CU_{12}N_{84}O_2$ (Mw=3562.6 g/mol): C38.43, H3.25, N33.02. Found: C38.55, H3.23, N32.51.

Example 2

In order to demonstrate the functionality of metal-organic frameworks featuring coordinatively-unsaturated metal centers for separating gases, a mmen-CuBTTri framework as shown in FIG. 1 was constructed and tested.

The mmen-CuBTTri and men-CuBTTri adsorbents were initially tested in the context of separating a mixture stream including $CO_2$ and $N_2$ to obtain a stream richer in $N_2$ as compared to the mixture stream, with the adsorption of $CO_2$ in the frameworks at low pressures.

Gas adsorption isotherms for pressures in the range 0-1.1 bar were measured by a volumetric method using a Micromeritics ASAP2020 instrument. A sample was transferred in an $N_2$ filled glovebag to a pre-weighed analysis tube, which was capped with a transeal and evacuated by heating (50° C. for mmen-CuBTTri, 100° C. for men- CuBTTri) under dynamic vacuum for 24 hours. The evacuated analysis tube containing the degassed sample was then carefully transferred to an electronic balance and weighed again to determine the mass of sample (108.5 mg for mmen-, 69.2 mg for men-CuBTTri). The tube was then transferred back to the analysis port of the gas adsorption instrument. For all isotherms, warm and cold free space correction measurements were performed using ultra-high purity Helium gas (UHP grade 5.0, 99.999% purity); $N_2$ isotherms at 77 K were measured in liquid nitrogen using UHP-grade gas sources. $CO_2$ and $N_2$ isotherms at 298, 308 and 318 K were measured using a Julabo isothermal bath with UHP-grade gases. Oil-free vacuum pumps and oil-free pressure regulators were used for all measurements to prevent contamination of the samples during the evacuation process or of the feed gases during the isotherm measurements.

Figure 2A:
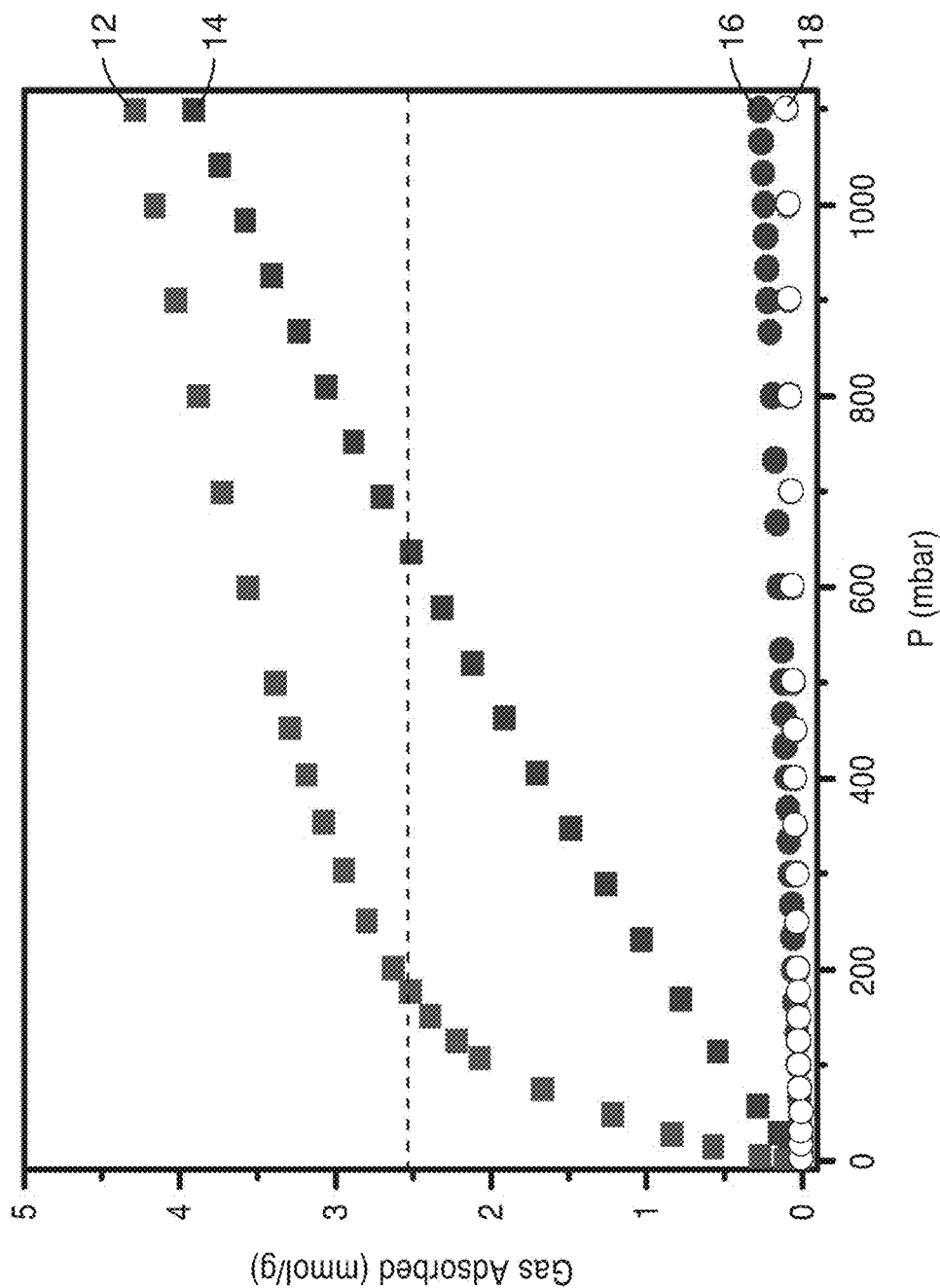
FIG. 2A is a graph plotting gravimetric gas sorption isotherms for $CO_2$ (squares) and $N_2$ (circles) adsorption at 25° C. for mmen-CuBTTri and CuBTTri. The horizontal dashed line in corresponds to 10 wt % $CO_2$ adsorption.
Figure 2B:
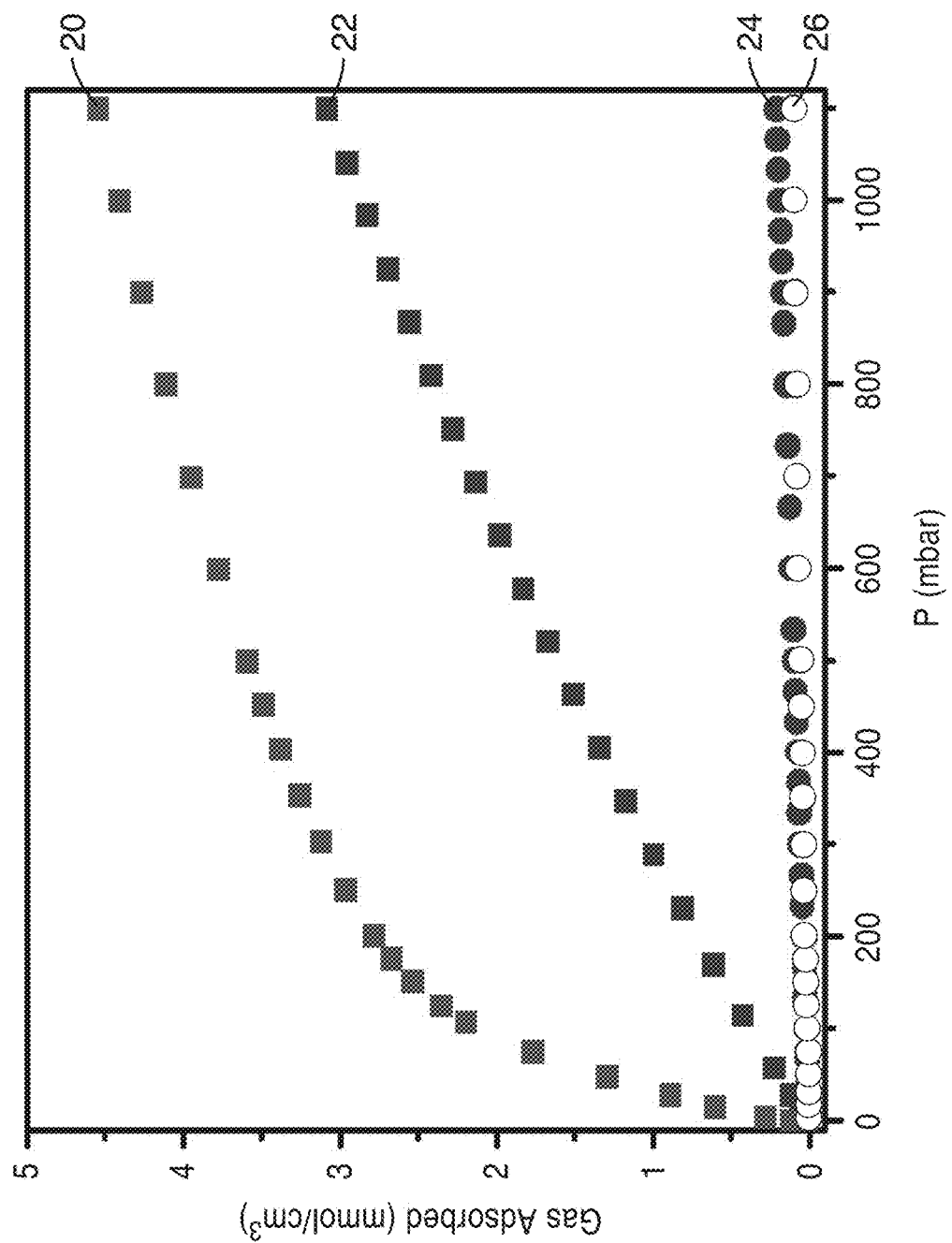
FIG. 2B is a graph plotting volumetric gas sorption isotherms for $CO_2$ (squares) and $N_2$ (circles) adsorption at 25° C. for mmen-CuBTTri and CuBTTri for comparison to FIG. 2A.

The incorporation of mmen in the CuBTTri framework resulted in a material with excellent $CO_2$ adsorption characteristics. As shown in FIG. 2A and FIG. 2B, mmen-CuBTTri displays significantly enhanced $CO_2$ adsorption at all pressures between 0 and 1.1 bar relative to the unappended framework.

Thermogravimetric analyses were carried out at a ramp rate of 1° C./min under a nitrogen flow with a TA Instruments TGA Q5000 V3.1 Build 246. $CO_2$ cycling experiments were performed using 15% $CO_2/N_2$ (Praxair Certified standard NI-CD15C-K) and $N_2$ (Praxair, 99.99%). A flow rate of 25 mL/min was employed for both gases. Prior to cycling, the sample was activated by heating at 60° C. for 1 hour, followed by cooling to 25° C. under an $N_2$ atmosphere. Sample mass was normalized to be 0% at 25° C. under an $N_2$ atmosphere. Masses were uncorrected for buoyancy effects, which were small compared to mass changes realized from gas adsorption.

The crystallite volumetric capacities of CuBTTri and mmen-CuBTTri were determined from unit cell densities. Only slight changes to the unit cell length were apparent from the PXRD diffraction patterns upon addition of mmen to the open-metal sites of CuBTTri. For both samples, a unit cell length of a=18.647 A and a unit cell volume of V=6483.8 A3 were used for density calculations. The molecular weight of mmen-CuBTTri was calculated to have 1 mmen for each open metal site, while CuBTTri was calculated to have no guest solvent molecules present. Gas sorption data was converted from mmol/g to mmol/cm$^3$ with the density of CuBTTri: p=0.789 g/cm$^3$ D and the density of mmen-CuBTTri: p=1.059 g/cm$^3$ Quantifying the extent of the improvement in $CO_2$ adsorption between CuBTTri and mmen-CuBTTri is not trivial, since the degree of improvement depends significantly on the units to which the gas uptake is normalized. FIG. 2A plots the gravimetric gas adsorption isotherm, while FIG. 2B plots the crystallite volumetric gas adsorption isotherm for the two materials.

FIG. 2A is a graph plotting gravimetric gas sorption isotherms for $CO_2$ (squares) 12 and $N_2$ (circles) 16 adsorption at 25° C. for mmen-CuBTTri. Gravimetric gas sorption isotherms for $CO_2$ (squares) 14 and $N_2$ (circles) 18 for adsorption at 25° C. for CuBTTri alone is also plotted for comparison. The horizontal dashed line in corresponds to 10 wt % $CO_2$ adsorption.

FIG. 2B is a graph plotting volumetric gas sorption isotherms for $CO_2$ (squares) 20 and $N_2$ (circles) 24 adsorption at 25° C. for mmen-CuBTTri. Volumetric gas sorption isotherms for $CO_2$ (squares) 22 and $N_2$ (circles) 26 adsorption at 25° C. for CuBTTri alone is also plotted for comparison for comparison to FIG. 3A.

The volumetric capacity for an actual adsorber unit is dependent upon how crystallites pack together and the fraction of void space within the occupied volume. Yet, gravimetric capacity alone does not provide a complete measure of the performance of a material being proposed for stationary applications, such as post-combustion $CO_2$ capture. Here, infrastructure costs are linked more directly to the volume the adsorbent would occupy than to its mass. Because incorporation of mmen into CuBTTri increases the framework density by 34% with no significant change in volume, this system is a good candidate for comparisons between gravimetric and volumetric capacities.

It is important to note, however, that no single-crystal diffraction data are available for either CuBTTri or mmen-CuBTTri. Framework volumes are based upon powder pattern unit cell optimizations, and framework compositions are based upon elemental and thermogravimetric analyses.

At 25° C. and 1 bar, mmen-CuBTTri adsorbs 4.2 mmol/g of $CO_2$ (15.4 wt %), representing a 15% improvement in gravimetric capacity compared to the unmodified CuBTTri framework. However, $CO_2$ comprises at most 15% of coal fired power station flue gas and the effluent is released into the environment at total pressures near 1 bar. Thus, the more important criterion for $CO_2$ capacity is that of the framework at a pressure near 0.15 bar. At 25° C. and 0.15 bar of $CO_2$, mmen-CuBTTri adsorbs 2.38 mmol/g (9.5 wt %). Note that 2.90 mmol/g would correspond to the adsorption of one $CO_2$ molecule per mmen in the functionalized framework. Under the same conditions, the unmodified framework only adsorbs 0.69 mmol/g (2.9 wt %). Thus, on a gravimetric basis, mmen-CuBTTri adsorbs nearly 3.5 times as much $CO_2$ at the relevant pressures. Volumetrically, however, mmen-CuBTTri adsorbs about 4.7 times more $CO_2$ at 0.15 bar than CuBTTri. The difference between gravimetric and volumetric densities is a direct consequence of the increased mass of the appended framework over the unappended material.

At 25° C., mmen-CuBTTri adsorbs less $N_2$ than CuBTTri at all pressures between 0.0 and 1.1 bar. This is due to the reduction in specific surface area upon incorporation of mmen, with the BET surface area of 870 m$^2$/g for mmen-CuBTTri being roughly half of the 1770 m$^2$/g observed for CuBTTri. The additional polarizing sites in mmen-CuBTTri enhance $N_2$ adsorption less than the decreased surface area diminishes $N_2$ adsorption. The opposite trend was observed for $CO_2$ adsorption. Enhanced adsorption of only one gas is a defining characteristic of chemisorption. In contrast, frameworks replete with open metal cation sites can be expected to polarize all gases more effectively, including $N_2$, accounting for the substantially greater $N_2$ adsorption in Mg$_2$(dobdc) relative to mmen-CuBTTri.

The selectivity (S) for adsorption of $CO_2$ over $N_2$ in mmen-CuBTTri was estimated from the single-component isotherm data. For $CO_2$ capture, this value typically reports the ratio of the adsorbed amount of $CO_2$ at 0.15 bar to the adsorbed amount of $N_2$ at 0.75 bar; the value is normalized for the pressures chosen. The values are derived from an approximate flue gas composition of 15% $CO_2$, 75% $N_2$, and 10% other gases, at a total pressure of 1 bar. Pure-component isotherm selectivities, which frequently are calculated from the excess adsorption data directly measured by gas adsorption, can be misleading. The adsorption selectivity, $S_{IAST}$, was therefore modeled by applying the Ideal Adsorbed Solution Theory (IAST) to the calculated absolute adsorption isotherms. The accuracy of the IAST procedure has been established for the adsorption of a wide variety of gas mixtures in different zeolites, as well as $CO_2$ capture in metal-organic frameworks. For mmen-CuBTTri, SIAST values were calculated to be 327, 200, and 123 at 25° C., 35° C., and 45° C., respectively. The selectivity that was observed at 25° C. is one of the highest values reported for a metal-organic framework.

Example 3

To further characterize the mmen-CuBTTri frameworks, the isosteric heat of adsorption and working capacity of the materials were analyzed. Utilizing a dual-site Langmuir adsorption model, isosteric heats of adsorption were calculated for $CO_2$ in mmen-CuBTTri and compared to those obtained from data for bare CuBTTri, which were fit using a single-site Langmuir model to give a value of −24 kJ/mol. The $N_2$ adsorption isotherm for mmen-CuBTTri was also fit to a single-site Langmuir model, resulting in a calculated isosteric heat of adsorption of −15 kJ/mol.

The isosteric heat of $CO_2$ adsorption in mmen-CuBTTri approaches −96 kJ/mol at zero coverage, corresponding to the largest value yet reported for $CO_2$ adsorption in a metal-organic framework. For comparison to mmen-CuBTTri, the heat of adsorption for en-CuBTTri was recalculated with the same dual-site Langmuir model. Because this model incorporates absolute adsorption, direct comparisons between the two different models are not possible. From the dual-site Langmuir model, the isosteric heat of $CO_2$ adsorption in en-CuBTTri was calculated to be −78 kJ/mol at zero coverage, nearly 20 kJ/mol lower in magnitude than the heat calculated for mmen-CuBTTri. Preferably, the isosteric heat of $CO_2$ adsorption of the material is greater than −70 kJ/mol at zero coverage as determined by the Clausius-Clapeyron relation.

Accordingly, mmen-CuBTTri has a significantly larger number of free amines available to bind guest $CO_2$ molecules. Because isosteric heats correspond to the average of all adsorption sites potentially populated at a specific coverage level, at zero coverage there is a higher probability of the $CO_2$ molecule adsorbing onto an amine in mmen-CuBTTri compared with en-CuBTTri.

Despite the large binding enthalpy between alkylamines and $CO_2$, the substantial decrease in the $-Q_{st}$ data with loading indicates that many weaker adsorption sites are also being sampled by the $CO_2$ molecules under the conditions probed. While amine sterics may play a role in the improved adsorption properties of mmen-CuBTTri, it is not possible to make comparisons between isosteric heats of adsorption as a function of amine sterics because of the differences in amine loading levels.

The significantly greater working capacities of strongly binding adsorbents may lead to materials that are less expensive to operate than those that have smaller working capacities. Solid adsorbents with large isosteric heats of adsorption have considerable advantages including high selectivity and high capacity for $CO_2$ at low partial pressures; however, they are often believed to be the most difficult to regenerate. Regeneration, however, is very dependent on the method best suited to a given material. For carbon capture from flue gas streams, vacuum and temperature swing adsorption methodologies are the ones most frequently envisioned. Vacuum swing adsorption can best be approximated by the difference in capacities between the adsorption and desorption pressures. For mmen-CuBTTri, a 7 wt % working capacity between 0.15 and 0.02 bar at 25° C. was calculated. For temperature swing methods, adsorbents with high heats of adsorption may prove to be better candidates than materials with moderate heats of adsorption. This is because the capacities of adsorbents with high heats of adsorption are more dependent on temperature than materials with smaller heats of adsorption.

Figure 7:
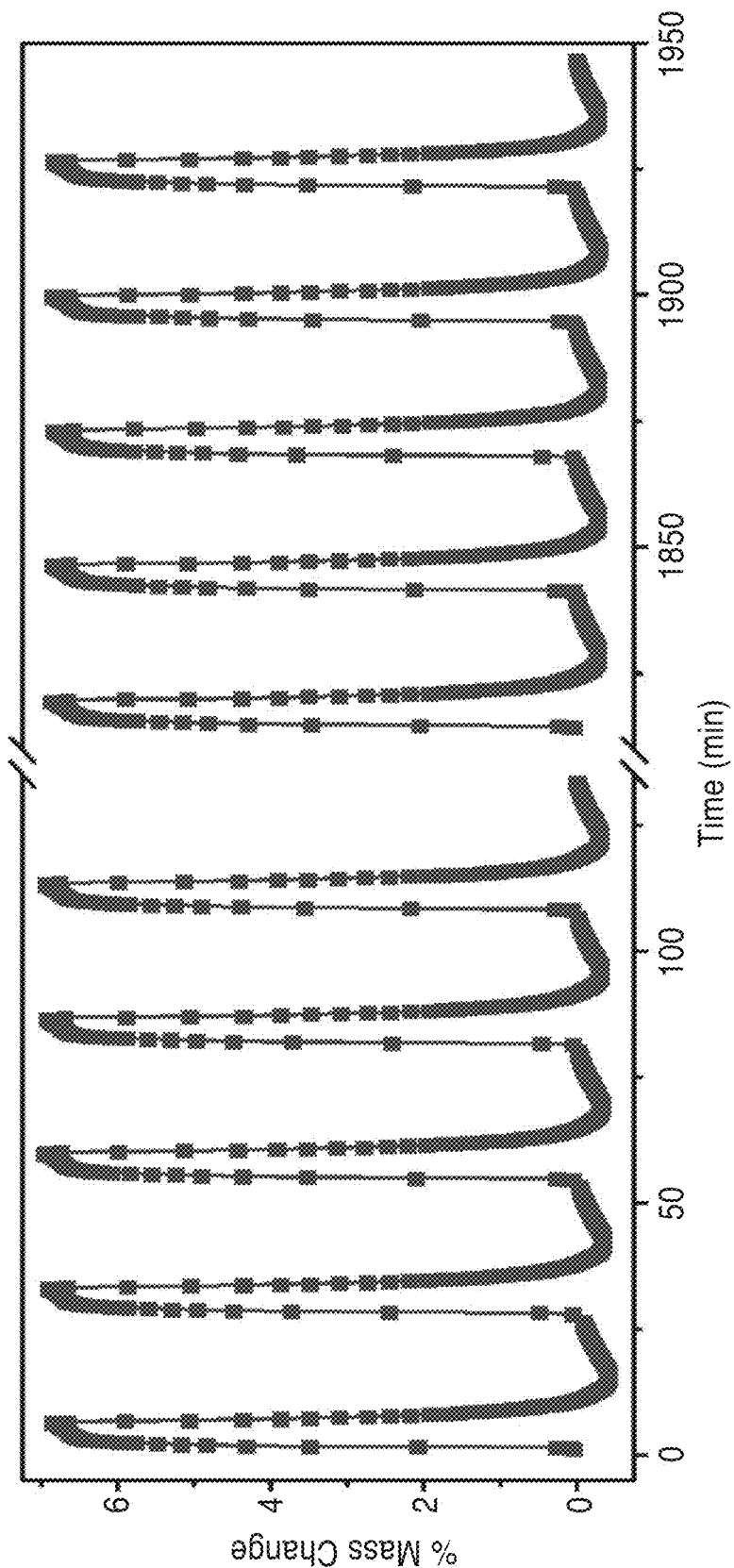
FIG. 7 is a graph of % mass change over time with repeated adsorption cycles. Upon introduction of a 15% $CO_2$ mixture in $N_2$ at 25° C., the mass of mmen-CuBTTri increased by nearly 7% as measured by thermogravimetric analysis. Upon saturation, a $N_2$ purge flow with a temperature swing to 60° C. fully regenerated the material, with no apparent capacity loss after 72 cycles.

The cyclability of the mmen-CuBTTri material as a $CO_2$ adsorbent was evaluated using a combined temperature swing and nitrogen purge approach. Utilizing a thermogravimetric analyzer, a mixture of 15% $CO_2$ in $N_2$ was introduced into the furnace for 5 minutes at 25° C. It was observed that the sample mass increased by nearly 7% upon introduction of the mixed gas, due to strong adsorption of $CO_2$, even in the dilute mixture. The adsorbent was then regenerated by changing the flow to a pure $N_2$ stream followed by rapid ramping of the furnace at 5° C./min to 60° C. The sample was held for 2 minutes at 60° C., and then cooled at 5° C./min to 25° C. The temperature was allowed to stabilize for 2 minutes, followed by the reintroduction of the 15% $CO_2$ in $N_2$ mixture. The 27 minute cycling procedure was repeated 72 times, with no apparent change in capacity as shown in FIG. 7. The kinetics of the adsorption are sufficiently quick that little additional $CO_2$ is adsorbed after the first few minutes, and even shorter cycle times could be utilized with only small reductions in capacity. Similarly, complete desorption is realized prior to the end of each 2 minute isotherm. Importantly, the cycling capacity of mmen-CuBTTri under dry conditions is comparable to or even greater than the working capacity of a 30% MEA solution, which is frequently reported as 5.5 wt %.

Example 4

Heats of adsorption approaching −100 kJ/mol and highly specific interactions are indicative of chemisorptive processes. In the absence of water, it is believed that the electrophilic $CO_2$ molecule is accepting electron density from the lone pair of the free amine of mmen, forming a zwitterionic carbamate. Previous spectroscopic studies of $CO_2$ binding in amine containing metal-organic frameworks have investigated only less basic aromatic amines. For example, it was recently shown in $NH_2$-MIL-53(Al) that the amine was not directly interacting with the $CO_2$, but rather, other physisorptive processes account for the favorable adsorption characteristics of the material.

Diffuse Reflectance Infrared Fourier Transform Spectroscopy (DRIFTS) measurements were performed on mmen-CuBTTri using a high-pressure (0-3 bar) gas cell to confirm and characterize the proposed chemisorptive process. Infrared spectra were collected on a Perkin Elmer Spectrum 400 FTIR spectrometer equipped with an attenuated total reflectance accessory (ATR). For Diffuse Reflectance Infrared Fourier Transform Spectroscopy (DRIFTS) spectra, the FTIR spectrometer was equipped a Barrick Praying Mantis Diffuse Reflectance accessory and a high-pressure gas cell with temperature control. 5% $CO_2$ in Be (Praxair certified standard BE CD5C-K) and a vacuum were attached to the high-pressure cell. Gas was slowly introduced into an evacuated cell containing mmen-CuBTTri prepared in a $N_2$ filled glovebag. Maximum pressure delivered to the cell was 1.5 bar above atmospheric pressure. Following adsorption, the sample was regenerated at 60° C. under dynamic vacuum for two hours.

Figure 3:
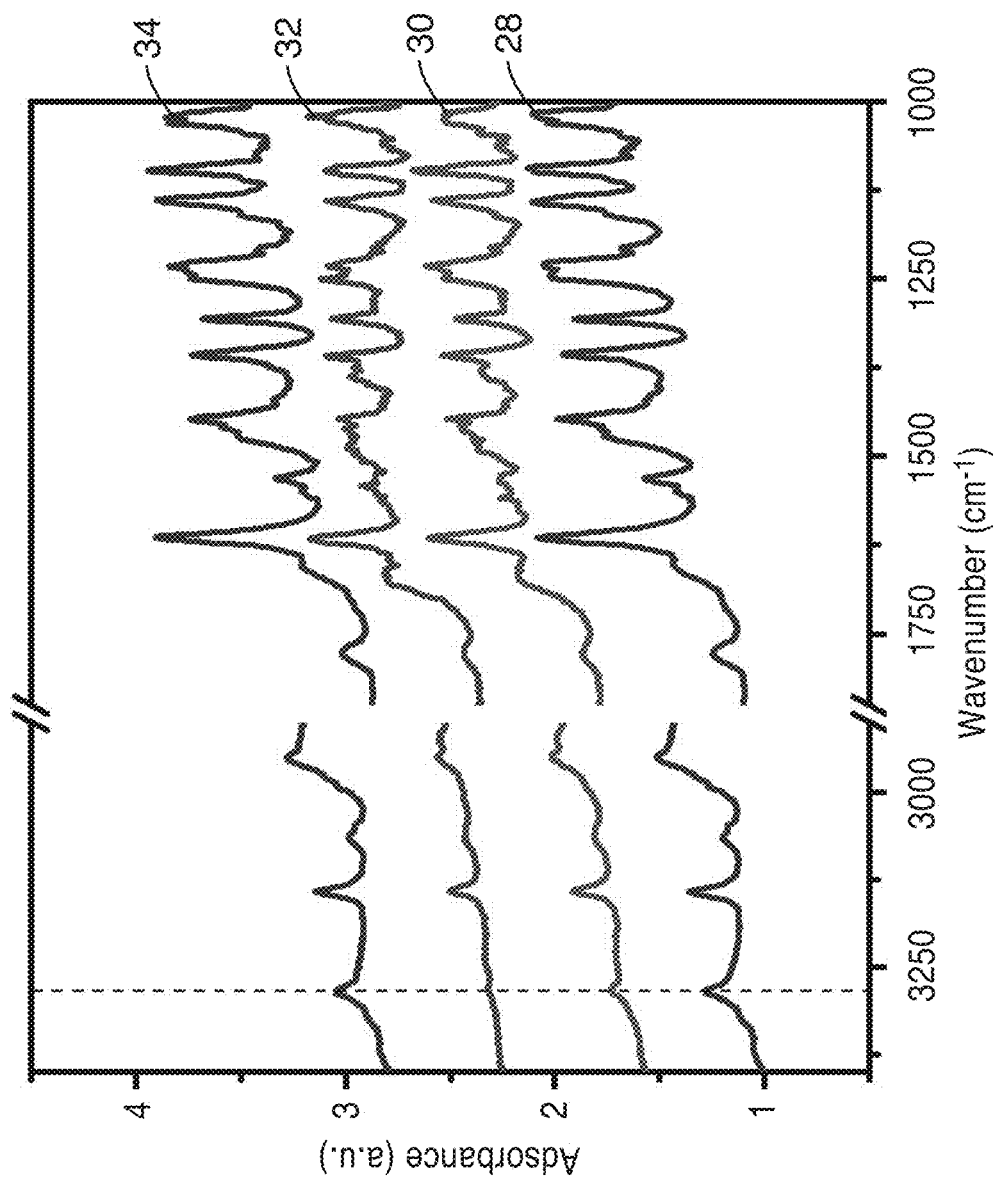
FIG. 3 is a graph of infrared spectra obtained upon exposure of mmen-CuBTTri to a 5% $CO_2$/95% He gas mixture in a high-pressure DRIFTS cell. Under dry conditions, the N—H stretch of mmen is apparent at 3283 $cm^{-1}$ (vertical dashed line) on a fully evacuated sample (28). Dilute $CO_2$ in He was slowly introduced into the cell (30) up to a dynamic pressure of 1.5 bar (32). Upon saturation, the N—H stretch fully disappeared. Following reactivation under vacuum and heating at 60° C. (34), the N—H stretch reappeared.

FIG. 3 plots the infrared absorbance of mmen-CuBTTri under various pressures of $CO_2$ in a 5% $CO_2$/95% He gas mixture in the high-pressure DRIFTS cell. Under dry conditions, the N-H stretch of mmen is apparent at 3283 $cm^{-1}$ (vertical dashed line) on a fully evacuated sample is shown at plot 28. The reported frequency for the N—H stretch in free mmen is 3279 $cm^{-1}$. Dilute $CO_2$ in He was slowly introduced into the cell at plot 30 up to a dynamic pressure of 1.5 bar at plot 32. Upon saturation, a total disappearance of the N—H band at 3283 cm$^{-1}$ is clearly observed with the introduction of 5% $CO_2$ in He in the cell at increasing pressures. Upon regeneration of the solid under vacuum and heating at 60° C. at plot 34, the N—H stretching band returned. A sharp band at 1386 cm$^{-1}$ also appears in the spectra as $CO_2$ is introduced; diffuse bands near 1669, 1487, and 1057 cm$^{-1}$ are also apparent in addition to changes in the fingerprint region.

Water was strictly excluded from the material for the DRIFTS measurements to eliminate the possibility of carbonate formation. Because the amines are tethered to the framework and well separated, we do not believe that it is possible for two amines to be concertedly interacting with a single $CO_2$ molecule. Similar measurements have been performed on other porous materials, most notably amine-grafted mesoporous silicas. In these materials, however, two amines can often act concertedly and the experiments frequently incorporated water vapor, making direct comparisons difficult. It has been previously reported, however, in dry amino acid-based ionic liquids that zwitterionic $CO_2$-species exhibit sharp infrared band near 1660 cm$^{-1}$. From the large calculated heat of adsorption and observed band changes in the infrared region upon $CO_2$ addition, it is believed that the primary mechanism of $CO_2$ adsorption at low pressures is the chemisorption of $CO_2$ gas onto mmen molecules resulting in the formation of zwitterioinc carbamates or carbamic acid.

Example 5

Figure 4:
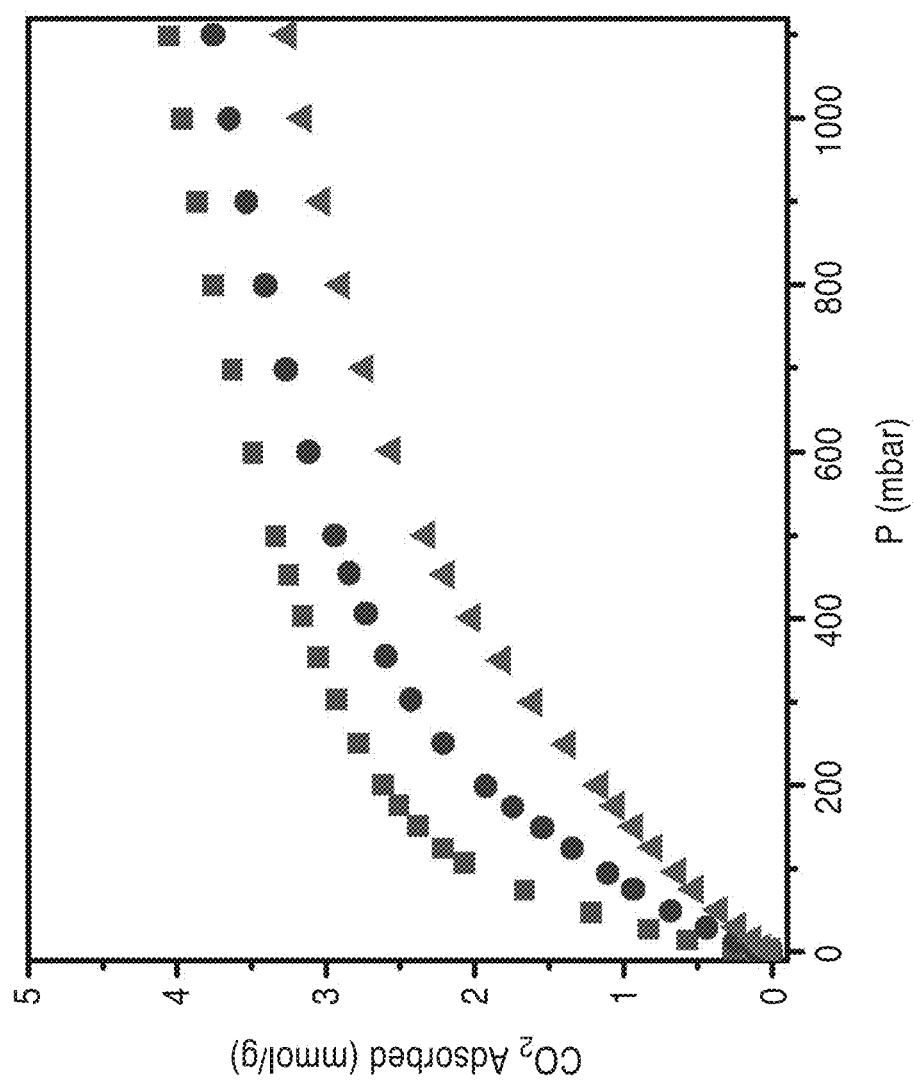
FIG. 4 is a graph of $CO_2$ adsorption isotherms at 298 K (squares), 308 K (circles) and 318 K (triangles) for mmen-CuBTTri.
Figure 5:
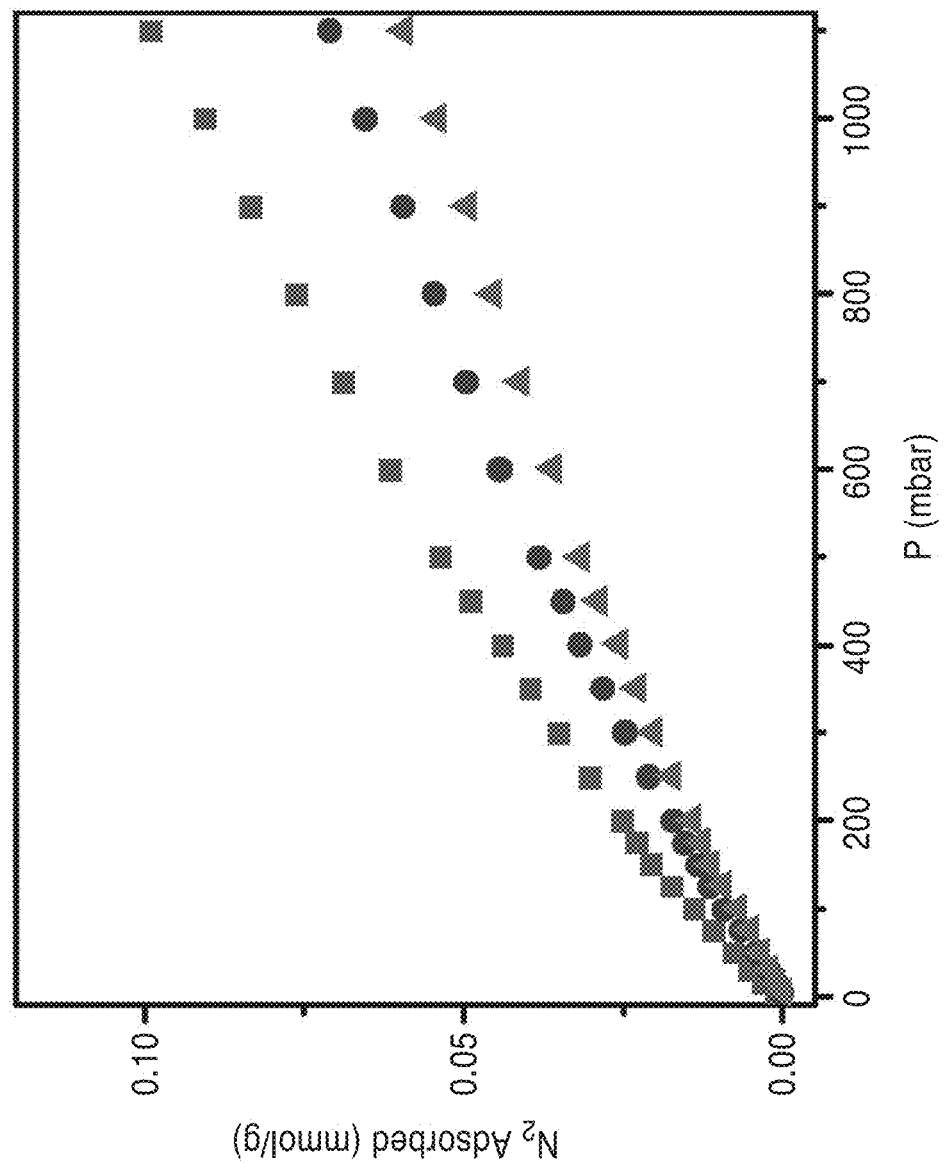
FIG. 5 is a graph of $N_2$ adsorption isotherms at 298 K (squares), 308 K (circles) and 318 K (triangles) for mmen-CuBTTri.

The steric effect upon diamine incorporation was also evaluated. The framework CuBTTri was additionally modified with N methylethylenediamine (men), an asymmetric diamine with one primary and one secondary amine. The adsorption isotherms of mmen-CuBTTri for $CO_2$ at 298 K (squares), 308 K (circles) and 318 K (triangles) is shown in FIG. 4 as a baseline for comparison. FIG. 5 shows $N_2$ adsorption isotherms at 298 K (squares), 308 K (circles) and 318 K (triangles) temperatures for mmen-CuBTTri.

Relative to the performance of mmen-CuBTTri, men-CuBTTri performs more similarly to en-CuBTTri, for which only a small enhancement in $CO_2$ uptake was observed at very low pressures. A small improvement in performance was, however, realized through the use of men over en.

The significantly greater adsorption of $CO_2$ in mmen-CuBTTri is attributable to the larger number of amines that are accessible to guest $CO_2$ molecules. There are two primary factors affecting the incorporation of primary amines into CuBTTri. First, the best fits to the elemental analysis data indicate at least two times as many diamine molecules were incorporated into mmen-CuBTTri versus the en- and men-analogues. A reasonable explanation for the higher incorporation of mmen into the framework is the formation of a weaker coordinate bond between the secondary amine on mmen and a framework $Cu^{2+}$ ion compared with the relatively stronger coordinate bond formed between a primary amine and a $Cu^{2+}$ ion. The significantly greater reversibility of mmen binding with $Cu^{2+}$ imparts it with a faster diffusion rate through the pores such that mmen molecules that bonded with copper sites near pore openings were labile in the hot hexane solution employed for grafting. These diamines were capable of migrating deeper into pores to achieve high surface coverage. In the case of primary amines, the irreversibility of the coordinate bond at the synthesis conditions surveyed severely limited the diffusion of en and men into the pores. Once appended, additional diamines could only diffuse through constricted pores to reach interior metal sites. Note that in men-CuBTTri, the primary amine end of men is coordinated to the metal centers while the sterically hindered secondary amine is available to interact with guest molecules in the pores. Increased reversibility of en and men binding was sought through the use of higher boiling solvents and lower concentrations; however, grafting temperatures that significantly exceeded 100° C. resulted in the decomposition of the framework.

Second, based upon the calculated heats of adsorption for en- and men-CuBTTri, the number of amines that were strongly adsorbing $CO_2$ was significantly less than the number of amines that were appended in each framework. This is because not all of the amines in the en- and men-frameworks bonded to open metal sites. Grafted amines severely reduced the pore diameters, slowing diffusion rates as previously discussed. Some of these pores then became blocked by the excess amines. Amines and other adsorption sites beyond these blockages were inaccessible to guest gases. This was confirmed by the low surface areas calculated for en- and men-CuBTTri. By comparison, the surface area for mmen-CuBTTri was significantly higher despite the greater number of total amines calculated to be within the framework.

Example 6

Figure 6:
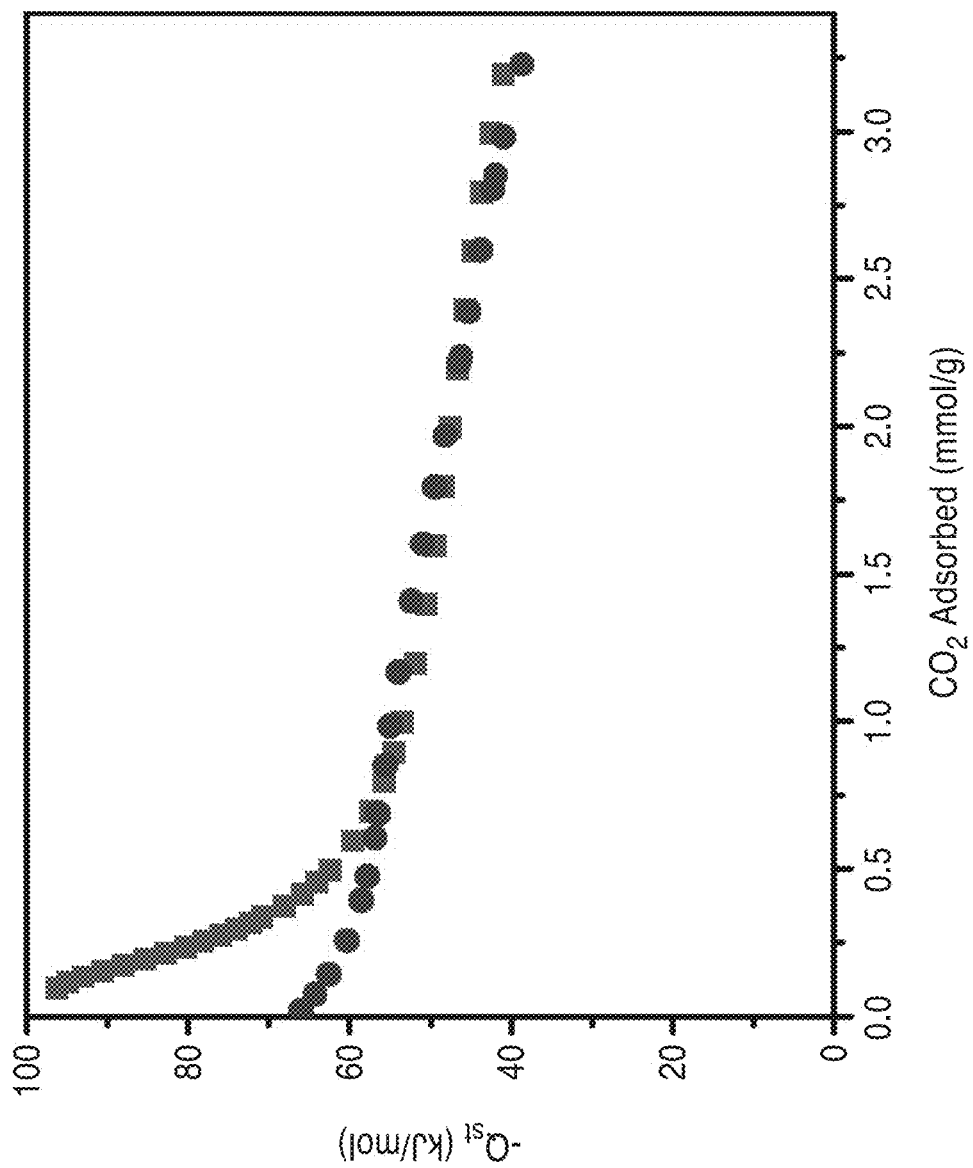
FIG. 6 is a graph of Isosteric heats of adsorption for mmen-CuBTTri calculated from the viral method (circles) and the dual-site Langmuir method (squares).

Isosteric heats of adsorption are commonly calculated after fitting adsorption equilibrium data to the Virial equation. FIG. 6 is a graph of isosteric heats of adsorption for mmen-CuBTTri calculated from the virial method (circles) and the dual-site Langmuir method (squares). FIG. 6 overlays the isosteric heats of adsorption calculated for mmen-CuBTTri using both the dual-site Langmuir and the Virial methods. At zero coverage, the Virial method gives a significantly lower magnitude for the heat of adsorption: −66 kJ/mol.

However, inflections in the isotherms tor mmen-CuBTTri are not accurately modeled with the Virial method. It is therefore believed that the values of the dual-site model are significantly more accurate at low $CO_2$ loadings. In contrast, at intermediate loadings there is good agreement between the dual-site Langmuir and Virial fits. While mmen-CuBTTri exhibits a large heat of adsorption at zero loading, heats of adsorption at intermediate loadings are also important for $CO_2$ capture. At a loading of 2.4 mmol/g, the approximate capacity of mmen-CuBTTri for $CO_2$ at 0.15 bar, the isosteric heat of adsorption was calculated to be about −45 kJ/mol by both the dual-site Langmuir and Virial models. Hence, in $CO_2$ capture applications, the average enthalpy of adsorption for $CO_2$ would be significantly less than the −96 kJ/mol value calculated for very low coverage levels. This has important implications for adsorbent regeneration.

The measured experimental data on pure component isotherms for $CO_2$ and $N_2$, in terms of excess loadings, were first converted to absolute loading using the Peng-Robinson equation of state for estimation of the fluid densities. The pore volume of mmen used for this purpose was 0.363 cm$^3$/g, based on the $N_2$ adsorption data at 77 K. The pore volume obtained was 51% that of bare CuBTTri.

The absolute component loadings were fitted with either a single-site Langmuir model or a dual-site Langmuir model. For $N_2$/mmen there are no discernible isotherm inflections and therefore the single-site Langmuir model was used for isotherm fitting. The single-site Langmuir model is also adequate for fitting the isotherm data for $CO_2$ in "bare" CuBTTri. In order to fit the experimental data for adsorption of $CO_2$ in mmen-CuBTTri, the dual-site Langmuir model was employed.

Due to their high surface areas and low bulk densities, these materials demonstrate remarkable working capacities for sequestering carbon dioxide, making them ideal for use in large scale processing plants and a great improvement over current adsorbents. The successful implementation of these new adsorbents could both reduce the substantial energy cost of hydrogen purification and reduce or eliminate $CO_2$ emissions in the generation of electricity from coal or syngas.

Example 7

To further demonstrate the broad functionality of the metal-organic framework family $M_2$(dobpdc) (M=Mg, Mn, Fe, Co, Cu, and Zn), the framework was used for the separation of $CO_2$ from mixed nitrogen gases. The $M_2$(dobpdc) structure type features approximately 18 Å-wide channels and exhibits exceptional $CO_2$ adsorption properties upon functionalization with mmen. Several different metal organic frameworks were prepared for comparison testing.

Referring to FIG. 8A and FIG. 8B, one synthesis scheme for the mmen-$M_2$-(dobpdc) functionalized framework is illustrated. As shown schematically in FIG. 8A, the initial framework is produced from $H_4$dobpdc (4,4'-Dihydroxy-(1,1'-biphenyl)-3,3'-dicarboxylic Acid). $H_4$dobpdc was produced by adding 4,4"-dihydroxybiphenyl (1.16 g, 6.24 mmol), $KHCO_3$ (2.00 g, 20.0 mmol), dry ice (4 g), and 1,2,4-trichlorobenzene (3 mL) to a PTFE insert within a steel acid digestion bomb (23 mL) and heated at 255° C. for 17 hours. After cooling to room temperature, the mixture was collected via vacuum filtration and washed with diethyl ether. The solid was suspended in 300 mL of distilled water, and filtered again. To the filtrate, neat HCl was slowly added until a pH between 1 and 2 was reached. The resulting crude product was collected via filtration. Recrystallization using 50 mL of acetone and 50 mL of water per gram of crude material afforded 0.68 g (40%) of pure product as a white powder.

Reaction of $H_4$dobpdc with $ZnBr_2 \cdot 2H_2O$ or $MgBr_2 \cdot 6H_2O$ in 1:1 DEF:EtOH produces $Zn_2$(dobpdc)(DEF)$_2 \cdot$DEF$\cdot H_2O$ (DEF-1) and $Mg_2$(dobpdc)(DEF)$_2 \cdot$DEF$_{1.5} \cdot H_2O$ (DEF-2), respectively as seen in FIG. 8A. DEF-1 was produced by mixing $H_4$dobpdc (4.0 mg, 0.015 mmol), $ZnBr_2 \cdot 2H_2O$ (8.9 mg, 0.034 mmol), and 0.5 mL of mixed solvent (1:1 DEF:EtOH; DEF=N,N'-diethylformamide) a 2-mL Pyrex tube. The tube was sealed and placed in a preheated oven at 100° C. After 72 hours, needle-shaped, colorless crystals had formed. The crystals were isolated by filtration and washed with hot DEF to afford 3.7 mg (35%) of product.

Similarly, DEF-2 was produced by loading $H_4$dobpdc (24 mg, 0.088 mmol), $MgBr_2 \cdot 6H_2O$ (60 mg, 0.21 mmol), and 3 mL of solvent (1:1 DEF:EtOH) into a 10 ml Pyrex cell and sealed with a PTFE cap. The mixture was irradiated in a microwave reactor (CEM Discover) for 30 minutes at 120° C. After 30 minutes, the solution was cooled and the resulting solid was collected via filtration and washed with hot DEF. The solid was dried under vacuum to yield 57.5 mg (95%) of product as a white powder.

Upon exposure of DEF-2 to atmospheric air, the white powder turns blue. Amine functionalization, however, appears to enhance framework stability, because no similar degradation was observed for mmen-2 upon exposure to air for one week.

In the crystal structure of DEF-1, four different dobpdc$^{4-}$ ligands and one DEF molecule are bonded to each $Zn^{2+}$ ion in a distorted octahedral geometry. There are three unique O donor types from the dobpdc$^{4-}$ ligand: bridging ($\mu_2$) aryloxide O atoms (O1), bridging ($\mu_2$) carboxylate O atoms (O2), and non-bridging carboxylate O atoms (O3). The equatorial plane of each $Zn^{2+}$ is composed of two trans-disposed O1 ligands from different linkers, one O3 donor atom, and one O2 donor atom. An O2 donor atom occupies one axial coordination site, while the other axial site is occupied by an O donor atom from DEF, the reaction solvent. This coordination mode results in the formation of helical chains of $Zn^{2+}$ atoms running along the c axis of the crystal. The resulting framework consists of a honeycomb lattice of hexagonal, one-dimensional channels approximately 18 Å in width. Bound DEF molecules occupy the $Zn^{2+}$ coordination sites along the corners of hexagonal channel walls. Powder X-ray diffraction (PXRD) data indicate DEF-2 to be isostructural with DEF-1.

Heating DEF-1 or DEF-2 at 420° C. for 65 minutes in vacuo yielded the fully activated adsorbent $Mg_2$(dobpdc) or $Zn_2$(dobpdc) respectively. Heating DEF-2 at 420° C. for 65 min under dynamic vacuum, removed the DEF molecules bound to the metal atoms, completely activating the material and generating open $Mg^{2+}$ coordination sites. Such extreme thermal treatment was necessary because soaking in methanol at 100° C. for 20 hours did not lead to exchange of the bound DEF molecules. The porosity of activated DEF-2 was confirmed via $N_2$ adsorption at 77 K, resulting in a BET surface area of 3270 m$^2$/g. Note that, in line with the expanded structure, this is significantly greater than the BET surface area of 1495 m$^2$/g reported for $Mg_2$(dobdc).

The synthesis and structure of mmen-$Mg_2$(dobpdc) or mmen-2 is depicted schematically at the right of FIG. 8A and FIG. 8B. An activated sample of DEF-1 of DEF-2 was suspended in hexanes and an excess of mmen was added. Specifically, a 77 mg, 0.24 mmol sample of activated DEF-2 was immersed in anhydrous hexane, and 20 equivalents of NAP-dimethylethylenediamine (mmen, 0.53 mL, 4.8 mmol) was added. The suspension was stirred for one day, filtered, and rinsed copiously with hexanes. The solid was then evacuated of residual solvents at 100° C. for 24 h to afford 87 mg (77%) of product as a gray-white powder.

As shown by powder X-ray diffraction, framework crystallinity was not significantly affected by activation or subsequent amine functionalization. A much reduced BET surface area of 70 m$^2$/g was calculated for mmen-2, while DFT pore size distributions indicated a reduction in average pore size.

Example 8

$CO_2$ adsorption isotherms were taken of the mmen-2 functionalized frameworks and the bare $Mg_2$(dobpdc) framework for comparison. Isosteric heats of adsorption for $Mg_2$(dobpdc) were calculated to be −44 kJ/mol at low coverage. This value is 42 kJ/mol higher in magnitude than the −42 kJ/mol previously reported for the analogous $Mg_2$(dobdc) framework.

The adsorption capacity of $Mg_2$(dobpdc) at 25° C. is 4.85 mmol/g (13.8 wt %) and 6.42 mmol/g (20.0 wt %) at 0.15 and 1 bar, respectively. The capacity of $Mg_2$(dobpdc) for $CO_2$ at 0.15 bar exceeds the capacity of most metal-organic frameworks.

The alkylamine-functionalized metal-organic framework mmen-2 displayed an extremely high affinity for $CO_2$ at extraordinarily low pressures. The $CO_2$ adsorption isotherms obtained at 25, 50, and 75° C. are presented in FIG. 9. At 25° C. and 0.39 mbar, near the current partial pressure of $CO_2$ in Earth's atmosphere, the compound adsorbed 2.0 mmol/g (8.1 wt %), which is 15 times the capacity of $Mg_2$(dobpdc). At the much higher pressure of 5 mbar, the median partial pressure of $CO_2$ within the International Space Station, the framework adsorbed 2.6 mmol/g (10.3 wt %). For comparison, zeolite 5A, which is currently used aboard the station to adsorb $CO_2$, adsorbs 0.85 mmol/g (3.6 wt %, crystallographic volumetric capacity 1.3 mmol/cm$^3$) at 5 mbar.

At 25° C., the $CO_2$ adsorption in mmen-2 reaches 3.14 mmol/g (12.1 wt %) at 0.15 bar and 3.86 mmol/g (14.5 wt %) at 1 bar. Remarkably, its $CO_2$ uptake at 1 bar and 25° C. exceeds the amount of $N_2$ adsorbed at 77 K. Thus, the low surface area measured at 77 K does not appear to accurately reflect the surface area accessible to $CO_2$. On a per mass basis, the amine-functionalized framework adsorbed less $CO_2$ than $Mg_2$(dobpdc) at pressures higher than ca. 0.1 bar. While the decreased surface area of mmen-2 may limit its capacity at super-atmospheric pressures, the large density difference between the two frameworks is primarily responsible for the lower gravimetric capacity of mmen-2. Crystallographic densities of 0.58 and 0.86 g/cm$^3$ were calculated for $Mg_2$(dobpdc) and mmen-2, respectively. For adsorbents of the same structure and widely different densities, volumetric capacities better represent $CO_2$ adsorption performance. At 0.15 bar, $Mg_2$(dobpdc) and mmen-2 adsorb 2.1 and 2.7 mmol/cm$^3$, respectively, while at 1 bar, the capacities of both adsorbents are 3.3 mmol/cm$^3$.

For stationary applications like CCS, the greater volumetric capacity of mmen-2 makes it the superior adsorbent. Based upon the calculated number of dangling amine groups in mmen-2, a loading of 3.4 mmol/g would correspond to one $CO_2$ per amine, yet uptake of only ca. 2.2 mmol/g was observed. Here, pore blockages, hydrogen bonded amines, or cooperative binding mechanisms between two amines and one $CO_2$ may be limiting the accessible stoichiometry of mmen-2. Thus, significant additional capacity improvements might be realized in the material if conditions can be identified for appending one mmen per magnesium and binding one $CO_2$ molecule per dangling amine.

Isosteric heat of adsorption calculations were hindered by the presence of a prominent step in the isotherms at low pressures and convex to the pressure axis. Generally, continuous mathematical functions are used to model experimental isotherms, which then become the input parameters for the Clausius-Clapeyron relation. Since mathematical modeling of the $CO_2$ isotherms of mmen-2 with continuous equations over the entire pressure range were unavailable, each isotherm was modeled with two Langmuir-Freundlich equations. Data sets corresponding to the adsorption regions before and after the steps were compiled and then modeled individually. Isosteric heats of adsorption for mmen-2 were calculated from the 25, 50, and 75° C. isotherm models. At low loadings, heats significantly lower than those expected for chemical adsorption of $CO_2$ onto an amine were calculated. However, calculated heats quickly approached and maintained a value of −71 kJ/mol, which likely corresponds to the chemical adsorption of $CO_2$ onto the free amine of mmen. Here, a carbamate with a weak C—N bond is probably formed through interaction the lone pair of the free amine of mmen and the electrophilic carbon of $CO_2$.

In situ diffuse reflectance infrared Fourier transform spectroscopy (DRIFTS) was employed to probe the chemical nature of adsorbed $CO_2$. At 25° C., 1 bar of 5% $CO_2$ in Helium was introduced into an air-tight gas cell containing a sample of activated mmen-2. The difference spectrum between mmen-2 under a 1 bar atmosphere and the activated framework under vacuum was obtained. A prominent loss peak was observed at 3316 cm$^{-1}$ and assigned to the NH stretch of free mmen-2, and is indicative of chemical adsorption of $CO_2$ onto amines. Gain bands observed at 1702 cm$^{-1}$ and 1531 cm$^{-1}$ likely correspond to carbamate C=O and CHN group stretches, respectively.

Recent work on alkylamine grafted silica surfaces have suggested that chemical adsorption of $CO_2$ onto alkylamines is not possible without neighboring amines or surface hydroxyl groups to stabilize the resulting carbamates; ammonium carbamates or surface bonded carbamates are formed, respectively. The formation of surface bonded carbamates in mmen-2 is unlikely due to a lack of surface hydroxyl groups, and the broad NH stretches expected for ammonium cations are not definitively resolvable from the DRIFTS difference spectrum. Furthermore, the slow reversibility of mmen-2 at room temperature appears to preclude the formation of ammonium carbamates, which have been reported to desorb $CO_2$ from primary amines readily at room temperature.

The step observed in each isotherm marks the pressure at which $CO_2$ adsorption becomes dominated by chemisorption. Interestingly, the step moves to significantly higher pressures as the adsorption temperature increases. The location of the step is modeled well by a simple Clausius-Clapeyron relation, which predicts how isotherms move as a function of temperature. The existence of the step, however, is unexpected in a strongly adsorbing material with large pores, and can best be explained by the surprising conclusion that weaker adsorption sites are energetically favored over amine adsorption sites at low coverage. This suggests that adsorption of $CO_2$ onto mmen is disfavored at low adsorptive concentrations (the density of gas phase $CO_2$ in the pores) because of the large positive entropy associated with reorganization of the amines, as required to form a chemical bond with $CO_2$.

Example 9

To evaluate the performance of mmen-2 as a regenerable adsorbent for $CO_2$ capture from air, thermogravimetric analysis (TGA) was utilized to monitor sample mass under dynamic environments. The changes in sample mass (normalized to the mass of the framework under $N_2$ at 25° C.) while simulated air containing 390 ppm $CO_2$ was flowed over the sample were obtained. Despite the very low concentration of $CO_2$, a 4.6% mc (% mc=percent mass change; 1.05 mmol/g; 4.4 wt %) was realized after 60 min.

Thermogravimetric analyses were carried out at ramp rates between 5 and 10° C./min under a nitrogen flow with a TA Instruments TGA Q5000 (Ver. 3.1 Build 246) or a Scinco TGA N-1000. Carbon dioxide cycling experiments were performed using a 15% $CO_2$ in $N_2$ (Praxair NI-CD15C-K), 390 ppm $CO_2$ in air (Praxair AI-CD-390C-K; 390 ppm $CO_2$, 21% $O_2$, balance N2), $CO_2$ (Praxair 99.998%) and $N_2$ (Praxair, 99.9%). A flow rate of 25 mL/minute was employed for all gases. Prior to cycling, the sample was activated by heating at 150° C. for 1 hour. The sample mass was normalized to be 0% at the adsorption temperature (25° C. for 390 ppm $CO_2$ and 40° C. for 15% $CO_2$) under flowing $N_2$ and sample mass was normalized to be 0% at 150° C. under flowing 100% $CO_2$.

The adsorbent was then regenerated under flowing $N_2$ at 150° C. for 30 minutes and the cycle repeated ten times with no apparent loss of capacity. The equilibrium capacity (2.0 mmol/g, 1.72 mmol/cm$^3$) of mmen-2 is similar to the capacities of the very best amine-grafted silica and alumina adsorbents reported to date. However, the kinetics of adsorption appear to be significantly faster in mmen-2 than for amines deposited via evaporation or polymerization methodologies. For example, while the pseudo-equilibrium capacity of an outstanding poly(ethyleneimine) impregnated silica gel was reported to be 2.4 mmol/g, it took nearly 200 minutes for the silica based adsorbent to realize $4.6\%_{mc}$, the capacity of mmen-2 for $CO_2$ after only 60 minutes. The easily accessed amines within mmen-2 appear to enhance adsorption rates greatly, enabling rapid adsorption-desorption cycles to be utilized.

Example 10

The capabilities of mmen-2 as an adsorbent for removing $CO_2$ from the flue gas of coal-fired power stations were also investigated. The dynamic cycling behavior of mmen-2 under the relevant, dry conditions: 15% $CO_2$ in $N_2$ flowing over the solid at 40° C. was also investigated.

After adsorbing $CO_2$ for 15 minutes, the sample was heated at 120° C. for 15 minutes under $N_2$. A capacity of $11.1\%_{mc}$ (2.52 mmol/g, 9.9 wt %) relative to the sample mass of mmen-2 under $N_2$ at 40° C. was realized. After 50 cycles, only a $0.2\%_{mc}$ capacity loss was observed. Longer adsorption and desorption times did not significantly improve the cycling capacity of the material, nor did higher desorption temperatures. It was noted that the apparent capacity of mmen-2 greatly exceeds the ca. 2 wt % working capacity of aqueous monoethanolamine (MEA) scrubbers, which would likely swing between the same adsorption and desorption temperatures.

If captured $CO_2$ is to be sequestered, high purity $CO_2$ is essential. To desorb the ca. 98% pure $CO_2$ adsorbed onto mmen-2, a $N_2$ or air purge cannot be utilized to strip the adsorbent bed. Hence, to approximate the working capacity of mmen-2 using a temperature swing without a $N_2$ purge, a pure $CO_2$ purge was utilized instead. A $7.8\%_{mc}$ (1.8 mmol/g, 7.2 wt %) was realized when 15% $CO_2$ in $N_2$ at 40° C. was desorbed with 100% $CO_2$ at 150° C.

From the discussion above it will be appreciated that the invention can be embodied in various ways, including the following:

1. An adsorption material, comprising: a porous metal-organic framework; and a plurality of ligands within the pores of the metal-organic framework, each ligand having at least one basic nitrogen group; wherein the basic nitrogen groups are configured to selectively adsorb $CO_2$ from a stream of mixed gases at pressures below approximately 3 bar and $CO_2$ partial pressures between approximately 1 and 1000 mbar.

2. The adsorption material of any previous embodiment, wherein the metal-organic framework is a framework selected from the group of frameworks consisting essentially of M-BTT where (M=Ca, Fe, Mn, Cu, Co, Ni, Cr, Cd) and (BTT=1,3,5-benzenetristetrazolate) and M-BTTri where (M=Cr, Mn, Fe, Co, Ni, Cu) and (BTTri=1,3,5-benzenetristriazolate).

3. The adsorption material of any previous embodiment, wherein the metal-organic framework is a framework selected from the group of frameworks consisting essentially of M-BTP where (M=Co, Ni, Zn) (BTP=1,3,5-benzenetrispyrazolate) and $M_3(BTC)_2$ where (M=Cu, Cr) and (BTC=1,3,5-benzenetriscarboxylate).

4. The adsorption material of any previous embodiment, wherein the metal-organic framework is a framework selected from the group of frameworks consisting essentially of MIL-100 where (M=Fe, Al, Cr, Ti, Sc, V) and Ligand=BTC=1,3,5-benzenetriscarboxylate) and MIL-101 (M=Fe, Al, Cr, Ti, Sc, V) and (Ligand=BDC=1,4-benzenedicarboxylate.

5. The adsorption material of any previous embodiment, wherein the metal-organic framework comprises $M_2$(dobdc) (M=Mg, Ca, Mn, Cr, Fe, Co, Ni, Cu, Zn) (dobdc=2,5-dioxido-1,4-benzenedicarboxylate).

6. The adsorption material of any previous embodiment, wherein the basic nitrogen group is incorporated into the framework on a ligand prior to framework formation.

7. The adsorption material of any previous embodiment, wherein the basic nitrogen group is incorporated into the framework through substitution or modification of a functional group that was bonded to a ligand prior to framework formation.

8. The adsorption material of any previous embodiment, wherein the basic nitrogen group is incorporated into the framework by substitution of a ligand after framework formation with the ligand with a basic nitrogen group.

9. The adsorption material of any previous embodiment, wherein the ligand comprises a first functional group reactive to metal atoms in the metal-organic framework and a second functional group reactive with carbon dioxide.

10. The adsorption material of any previous embodiment, wherein the first functional group of the ligand comprises a phenyl group.

11. The adsorption material of any previous embodiment, wherein the first functional group of the ligand comprises a carboxylate group, a triazolate group, a pyrazolate, a tetrazolates, a pyridine, or a sulfate.

12. The adsorption material of any previous embodiment, wherein the ligand comprises a primary alkylamine, a secondary alkylamine, a tertiary alkylamine, a primary imine, or a secondary imine.

13. The adsorption material of any previous embodiment, wherein the metal-organic framework comprises open metal sites and ligand occupied metal sites.

14. The adsorption material of any previous embodiment, wherein the adsorption material has an isosteric heat of $CO_2$ adsorption of greater than −60 kJ/mol at zero coverage using a dual-site Langmuir model.

15. A method of separating a mixture stream comprising $CO_2$ and $N_2$, the method comprising: contacting the mixture stream comprising $CO_2$ and $N_2$ with a material comprising a metal-organic framework, and a ligand with a basic nitrogen group; wherein the material has an isosteric heat of $CO_2$ adsorption of greater than −60 kJ/mol at zero coverage using a dual-site Langmuir model; obtaining a stream richer in $CO_2$ as compared to the mixture stream; and obtaining a stream richer in $N_2$ as compared to the mixture stream.

16. The method as recited in any previous embodiment, wherein the metal-organic framework is a framework selected from the group of frameworks consisting essentially of M-BTT where (M=Ca, Fe, Mn, Cu, Co, Ni, Cr, Cd) and (BTT=1,3,5-benzenetristetrazolate); M-BTTri where (M=Cr, Mn, Fe, Co, Ni, Cu) and (BTTri=1,3,5-benzenetristriazolate); M-BTP where (M=Co, Ni, Zn) (BTP=1,3,5-benzenetrispyrazolate); $M_3(BTC)_2$ where (M=Cu, Cr) and (BTC=1,3,5-benzenetriscarboxylate); MIL-100 where (M=Fe, Al, Cr, Ti, Sc, V) and Ligand=BTC=1,3,5-benzenetriscarboxylate); MIL-101 where (M=Fe, Al, Cr, Ti, Sc, V) and (Ligand=BDC=1,4-benzenedicarboxylate, and $M_2$(dobdc) (M=Mg, Ca, Mn, Cr, Fe, Co, Ni, Cu, Zn) where (dobdc=2,5-dioxido-1,4-benzenedicarboxylate).

17. The method as recited in any previous embodiment, wherein the ligand is selected from the group of ligands consisting essentially of a carboxylate group, a triazolate group, a pyrazolate, a tetrazolates, a pyridine, or a sulfate.

18. The method as recited in any previous embodiment, wherein the ligand comprises a primary alkylamine, a secondary alkylamine, a tertiary alkylamine, a primary imine, or a secondary imine.

19. A method of separating a mixture stream comprising $CO_2$ and other combustion gases, the method comprising: contacting the mixture stream comprising $CO_2$ and $N_2$ with a material comprising a metal-organic framework and a plurality of ligands that have at least one basic nitrogen group; obtaining a stream richer in $CO_2$ as compared to the mixture stream; and obtaining a stream richer in $N_2$ as compared to the mixture stream.

20. The method as recited in any previous embodiment, wherein the metal-organic framework and plurality of ligands comprises mmen-CuBTTri.

21. An adsorption material comprising: a metal-organic framework; and a ligand with a basic nitrogen group, wherein the adsorption material has an isosteric heat of $CO_2$ adsorption of greater than −80 kJ/mol at zero coverage using a dual-site Langmuir model.

22. The adsorption material of any previous embodiment, wherein the basic nitrogen group is incorporated into the framework on a ligand prior to framework formation.

23. The adsorption material of any previous embodiment, wherein the basic nitrogen group is incorporated into the framework through substitution or modification of a functional group that was bonded to a ligand prior to framework formation.

24. The adsorption material of any previous embodiment, wherein the basic nitrogen group is incorporated into the framework by substitution of a ligand after framework formation with the ligand with a basic nitrogen group.

25. The adsorption material of any previous embodiment, wherein the ligand comprises a carboxylate group, a triazolate group, a pyrazolate, a tetrazolates, a pyridine, or a sulfate.

26. The adsorption material of any previous embodiment, wherein the ligand comprises a primary amine, a secondary amine, a tertiary amine, a primary imine, or a secondary imine.

27. The adsorption material of any previous embodiment, wherein the metal-organic framework comprises open metal sites.

28. The adsorption material of claim 1, wherein the adsorption material has an isosteric heat of $CO_2$ adsorption of greater than −95 kJ/mol at zero coverage using a dual-site Langmuir model.

29. A method of separating a mixture stream comprising $CO_2$ and $N_2$ comprising: contacting the mixture stream comprising $CO_2$ and $N_2$ with a material comprising a metal-organic framework, and a ligand with a basic nitrogen group, wherein the material has an isosteric heat of $CO_2$ adsorption of greater than −80 kJ/mol at zero coverage using a dual-site Langmuir model; obtaining a stream richer in $CO_2$ as compared to the mixture stream; and obtaining a stream richer in $N_2$ as compared to the mixture stream.

Although the description above contains many details, these should not be construed as limiting the scope of the invention but as merely providing illustrations of some of the presently preferred embodiments of this invention. Therefore, it will be appreciated that the scope of the present invention fully encompasses other embodiments which may become obvious to those skilled in the art, and that the scope of the present invention is accordingly to be limited by nothing other than the appended claims, in which reference to an element in the singular is not intended to mean "one and only one" unless explicitly so stated, but rather "one or more." All structural, chemical, and functional equivalents to the elements of the above-described preferred embodiment that are known to those of ordinary skill in the art are expressly incorporated herein by reference and are intended to be encompassed by the present claims. Moreover, it is not necessary for a device or method to address each and every problem sought to be solved by the present invention, for it to be encompassed by the present claims. Furthermore, no element, component, or method step in the present disclosure is intended to be dedicated to the public regardless of whether the element, component, or method step is explicitly recited in the claims. No claim element herein is to be construed under the provisions of 35 U.S.C. 112, sixth paragraph, unless the element is expressly recited using the phrase "means for."

We claim:
1. A method of composite gas separations, the method comprising:
   (a) providing a mixture of gases for separation;
   (b) adsorbing acid gases from the mixture of gases on a porous metal-organic framework (MOF) adsorbent, the framework comprising:
      (i) a framework of $M_2$(dobpdc) where M is selected from the group of metals consisting of Mg, Ca, Mn, Cr, Fe, Co, Ni, Cu and Zn, the framework having coordinatively unsaturated metal centers; and
      (ii) a plurality of ligands disposed within pores of the metal-organic framework to produce a functionalized framework, said ligands having a ligand bridge with at least one first functional group capable of adsorbing a gas and at least one second functional group coupled to at least one metal center of said metal-organic framework;
      (iii) wherein contact of the functionalized framework with a volume of gases produces a stepped adsorption isotherm; and
      (iv) wherein gas adsorption properties before and after each step cannot be modeled as a continuous Langmuir function;
   (c) separating residual gases with reduced acid gas concentrations; and (d) releasing the adsorbed acid gases from the framework.

2. The method of claim 1, further comprising:
controlling metal-organic framework and gas mixture temperatures during adsorption; and
controlling pressure of the gas mixture during adsorption.

3. The method of claim 1, further comprising:
controlling metal-organic framework temperature during release of adsorbed acid gases from the metal-organic framework; and
controlling pressure of the metal-organic framework during the release of acid gases from the metal-organic framework.

4. The method of claim 1, further comprising:
purging the released acid gases from the metal-organic framework with a purge gas.

5. The method of claim 1, wherein said bridge of said ligand of said metal-organic framework comprises a molecule selected from the group of a linear alkane, a branched alkane, a linear alkene and a branched alkene.

6. The method of claim 1:
wherein said first functional group of said ligand of said metal-organic framework has a reactive atom that contains at least one lone pair of electrons selected from the group consisting of nitrogen, sulfur, and phosphorous; and wherein said ligand is reversibly bonded through a nitrogen, sulfur, or phosphorous atom to open metal sites of the framework.

7. The method of claim 1, wherein said first functional group of said ligand of said metal-organic framework comprises:

an oxygen containing group selected from the group consisting of alcohols, ethers and alkoxides;

wherein the ligand is reversibly bonded through an oxygen atom to open metal sites of the framework.

8. The method of claim 1, wherein said first functional group of said ligand of said metal-organic framework is selected from the group of carbenes, alkenes, and alkynes.

9. The method of claim 1, wherein said second functional group of said ligand of said metal-organic framework is selected from the group consisting of a primary alkylamine, a secondary alkylamine, and a tertiary alkylamine.

10. The method of claim 1, wherein said second functional group of said ligand of said metal-organic framework is selected from the group consisting of a primary imine and a secondary imine.

11. The method of claim 1, wherein said ligand of said metal-organic framework is selected from the group consisting of a Tetraethylenepentamine and a Diethylenetriamine.

12. The method of claim 1, wherein said ligand of said metal-organic framework is selected from the group consisting of Tris(2-aminoethyl)amine and Tris[2(methylamino)ethyl]amine.

13. The method of claim 1, wherein said ligand of said metal-organic framework comprises N,N'-dimethylethylenediamine (mmen).

14. The method of claim 1, wherein the metal-organic framework comprises both open metal sites and ligand occupied metal sites.

15. A method of composite gas separations, the method comprising:

(a) providing a mixture of gases for separation;
(b) adsorbing acid gases from the mixture of gases on a porous metal-organic framework (MOF) adsorbent, the framework comprising:

(i) a framework of $M_2$(dobpdc) where M is selected from the group of metals consisting of Mg, Ca, Mn, Cr, Fe, Co, Ni, Cu and Zn, the framework having coordinatively unsaturated metal centers; and (ii) a plurality of ligands disposed within pores of the framework, coupled to at least one metal center of said framework, to produce a functionalized framework, said ligands comprising at least two functional groups separated by a ligand bridge, each functional group having at least one reactive atom of nitrogen that contains one or more lone pairs of electrons;

(iii) wherein contact of the functionalized framework with a volume of gases produces a stepped adsorption isotherm; and (iv) wherein gas adsorption properties before and after each step cannot be modeled as a continuous Langmuir function;

(c) separating residual gases with reduced acid gas concentrations; and (d) releasing the adsorbed acid gases from the framework.

16. The method of claim 15, wherein said functional group of said ligand of said metal-organic framework is selected from the group consisting of a primary alkylamine, a secondary alkylamine, and a tertiary alkylamine.

17. The method of claim 15, wherein said functional group of said ligand of said metal-organic framework is selected from the group consisting of a primary imine and a secondary imine.

18. The method of claim 15, wherein said ligand of said metal-organic framework is selected from the group consisting of a Tetraethylenepentamine and a Diethylenetriamine.

19. The method of claim 15, wherein said ligand of said metal-organic framework is selected from the group consisting of Tris(2-aminoethyl)amine and Tris[2(methylamino)ethyl]amine.

20. The method of claim 15, wherein said ligand of said metal-organic framework comprises N,N'-dimethylethylenediamine (mmen).

21. The method of claim 15, wherein the metal-organic framework comprises open metal sites and ligand occupied metal sites.

* * * * *